(12) United States Patent
Greenburg et al.

(10) Patent No.: US 10,383,509 B2
(45) Date of Patent: *Aug. 20, 2019

(54) SYSTEM OF ACCESSORIES FOR USE WITH BRONCHOSCOPES

(71) Applicant: COVIDIEN LP, Mansfield, MA (US)

(72) Inventors: Benny Greenburg, Hod Hasharon (IL); Danny Blecher, Ramat Gan (IL); Gil Griefner, Ramat Gan (IL); Heinrich D. Becker, Schriesheim (DE)

(73) Assignee: COVIDIEN LP, Mansfield, MA (US)

( * ) Notice: Subject to any disclaimer, the term of this patent is extended or adjusted under 35 U.S.C. 154(b) by 634 days.

This patent is subject to a terminal disclaimer.

(21) Appl. No.: 14/804,698

(22) Filed: Jul. 21, 2015

(65) Prior Publication Data

US 2015/0342444 A1 Dec. 3, 2015

Related U.S. Application Data

(63) Continuation of application No. 10/571,793, filed as application No. PCT/IL2004/000843 on Sep. 14, 2004, now Pat. No. 9,089,261.

(Continued)

(51) Int. Cl.
*F16B 2/20* (2006.01)
*A61B 1/018* (2006.01)
(Continued)

(52) U.S. Cl.
CPC .......... *A61B 1/018* (2013.01); *A61B 1/0014* (2013.01); *A61B 1/0052* (2013.01);
(Continued)

(58) Field of Classification Search
USPC ....... 248/228.6, 228.7, 230.6, 230.7, 231.71, 248/231.81, 65, 70, 74.1, 74.2; 24/455,
(Continued)

(56) References Cited

U.S. PATENT DOCUMENTS 1,296,072 A * 3/1919 Gillespie .............. H01Q 1/1221
116/173
1,576,781 A 3/1926 Phillips
(Continued)

FOREIGN PATENT DOCUMENTS

CA 964149 3/1975
DE 3042343 A1 6/1982
(Continued)

OTHER PUBLICATIONS

United States Patent and Trademark Office, Office Action dated Apr. 22, 2005 in U.S. Appl. No. 10/491,099, 5 pages.
(Continued)

*Primary Examiner* — Alfred J Wujciak

(57) ABSTRACT

A clip or flexible handles extension facilitate simultaneous retention and operation of a bronchoscope and associated bronchoscopic tools held in one hand to allow operation by a single practitioner. Also provided is an adapter for the connection port of the working channel of a bronchoscope which performs both sealing and tool-locking functions. Also disclosed is a guide sheath arrangement with a reduced flexibility proximal portion to facilitate insertion of tools into the guide sheath.

11 Claims, 10 Drawing Sheets

Related U.S. Application Data

(60) Provisional application No. 60/564,944, filed on Apr. 26, 2004, provisional application No. 60/550,346, filed on Mar. 8, 2004, provisional application No. 60/502,615, filed on Sep. 15, 2003.

(51) Int. Cl.

| | | |
|---|---|---|
| A61B 1/00 | (2006.01) | |
| A61B 1/005 | (2006.01) | |
| A61B 1/012 | (2006.01) | |
| A61B 1/267 | (2006.01) | |
| A61B 90/57 | (2016.01) | |
| A61B 90/50 | (2016.01) | |
| A61B 90/53 | (2016.01) | |
| F16B 2/24 | (2006.01) | |

(52) U.S. Cl.
CPC ...... *A61B 1/00128* (2013.01); *A61B 1/00137* (2013.01); *A61B 1/00147* (2013.01); *A61B 1/012* (2013.01); *A61B 1/2676* (2013.01); *A61B 90/50* (2016.02); *A61B 90/53* (2016.02); *A61B 90/57* (2016.02); *F16B 2/20* (2013.01); *F16B 2/243* (2013.01)

(58) Field of Classification Search
USPC .......................... 24/456, 483, 484, 485, 531
See application file for complete search history.

(56) References Cited

U.S. PATENT DOCUMENTS

| | | | |
|---|---|---|---|
| 1,735,726 A | 11/1929 | Bornhardt | |
| 2,269,790 A * | 1/1942 | Sherrill | B01L 9/50 24/132 R |
| 2,407,845 A | 9/1946 | Nemeyer | |
| 2,650,588 A | 9/1953 | Drew | |
| 2,697,433 A | 12/1954 | Sehnder | |
| 2,826,206 A * | 3/1958 | Slater | B43K 23/001 131/257 |
| 3,016,899 A | 1/1962 | Stenvall | |
| 3,017,887 A | 1/1962 | Heyer | |
| 3,061,936 A | 11/1962 | Dobbeleer | |
| 3,073,310 A | 1/1963 | Mocarski | |
| 3,109,588 A | 11/1963 | Polhemus et al. | |
| 3,182,943 A * | 5/1965 | Crossman | B44D 3/123 248/210 |
| 3,191,652 A | 6/1965 | Benson et al. | |
| 3,294,083 A | 12/1966 | Alderson | |
| 3,301,513 A * | 1/1967 | Sugaya | F16L 3/24 248/228.6 |
| 3,310,264 A | 3/1967 | Appleton | |
| 3,341,909 A * | 9/1967 | Havener | B25B 5/101 24/350 |
| 3,367,326 A | 2/1968 | Frazier | |
| 3,439,256 A | 4/1969 | Kahne et al. | |
| 3,577,160 A | 5/1971 | White | |
| 3,614,950 A | 10/1971 | Rabey | |
| 3,644,825 A | 2/1972 | Davis, Jr. et al. | |
| 3,674,014 A | 7/1972 | Tillander | |
| 3,702,935 A | 11/1972 | Carey et al. | |
| 3,704,707 A | 12/1972 | Halloran | |
| 3,747,166 A | 7/1973 | Eross | |
| 3,821,469 A | 6/1974 | Whetstone et al. | |
| 3,868,565 A | 2/1975 | Kuipers | |
| 3,941,127 A | 3/1976 | Froning | |
| 3,983,474 A | 9/1976 | Kuipers | |
| 4,017,858 A | 4/1977 | Kuipers | |
| 4,024,997 A | 5/1977 | Kolpin | |
| 4,037,592 A | 7/1977 | Kronner | |
| 4,052,620 A | 10/1977 | Brunnett | |
| 4,054,881 A | 10/1977 | Raab | |
| 4,117,337 A | 9/1978 | Staats | |
| 4,173,228 A | 11/1979 | Van Steenwyk et al. | |
| 4,182,312 A | 1/1980 | Mushabac | |
| 4,202,349 A | 5/1980 | Jones | |
| 4,211,380 A * | 7/1980 | Lillegard | A61G 7/0503 24/328 |
| 4,228,799 A | 10/1980 | Anichkov et al. | |
| 4,256,112 A | 3/1981 | Kopf et al. | |
| 4,262,306 A | 4/1981 | Renner | |
| 4,287,809 A | 9/1981 | Egli et al. | |
| 4,298,874 A | 11/1981 | Kuipers | |
| 4,314,251 A | 2/1982 | Raab | |
| 4,317,078 A | 2/1982 | Weed et al. | |
| 4,319,136 A | 3/1982 | Jinkins | |
| 4,328,548 A | 5/1982 | Crow et al. | |
| 4,328,813 A | 5/1982 | Ray | |
| 4,339,953 A | 7/1982 | Iwasaki | |
| 4,341,220 A | 7/1982 | Perry | |
| 4,346,384 A | 8/1982 | Raab | |
| 4,358,856 A | 11/1982 | Stivender et al. | |
| 4,368,536 A | 1/1983 | Pfeiler | |
| 4,396,885 A | 8/1983 | Constant | |
| 4,396,945 A | 8/1983 | DiMatteo et al. | |
| 4,403,321 A | 9/1983 | Kruger | |
| 4,418,422 A | 11/1983 | Richter et al. | |
| 4,419,012 A | 12/1983 | Stephenson et al. | |
| 4,422,041 A | 12/1983 | Lienau | |
| 4,431,005 A | 2/1984 | McCormick | |
| 4,447,224 A | 5/1984 | DeCant, Jr. et al. | |
| 4,447,462 A | 5/1984 | Tafuri et al. | |
| 4,485,815 A | 12/1984 | Amplatz et al. | |
| 4,506,676 A | 3/1985 | Duska | |
| 4,543,959 A | 10/1985 | Sepponen | |
| 4,548,208 A | 10/1985 | Niemi | |
| 4,571,834 A | 2/1986 | Fraser et al. | |
| 4,572,198 A | 2/1986 | Codrington | |
| 4,583,538 A | 4/1986 | Onik et al. | |
| 4,584,577 A | 4/1986 | Temple | |
| 4,586,491 A | 5/1986 | Carpenter | |
| 4,607,619 A | 8/1986 | Seike et al. | |
| 4,608,977 A | 9/1986 | Brown | |
| 4,613,866 A | 9/1986 | Blood | |
| 4,617,925 A | 10/1986 | Laitinen | |
| 4,618,978 A | 10/1986 | Cosman | |
| 4,621,628 A | 11/1986 | Brudermann | |
| 4,625,718 A | 12/1986 | Olerud et al. | |
| 4,638,798 A | 1/1987 | Shelden et al. | |
| 4,642,786 A | 2/1987 | Hansen | |
| 4,645,343 A | 2/1987 | Stockdale et al. | |
| 4,649,504 A | 3/1987 | Krouglicof et al. | |
| 4,651,732 A | 3/1987 | Frederick | |
| 4,653,509 A | 3/1987 | Oloff et al. | |
| 4,659,971 A | 4/1987 | Suzuki et al. | |
| 4,660,970 A | 4/1987 | Ferrano | |
| 4,669,172 A | 6/1987 | Petruzzi | |
| 4,673,352 A | 6/1987 | Hansen | |
| 4,685,583 A | 8/1987 | Noon | |
| 4,688,037 A | 8/1987 | Krieg | |
| 4,701,049 A | 10/1987 | Beckman et al. | |
| 4,705,395 A | 11/1987 | Hageniers | |
| 4,705,401 A | 11/1987 | Addleman et al. | |
| 4,706,665 A | 11/1987 | Gouda | |
| 4,709,156 A | 11/1987 | Murphy et al. | |
| 4,710,708 A | 12/1987 | Rorden et al. | |
| 4,719,419 A | 1/1988 | Dawley | |
| 4,722,056 A | 1/1988 | Roberts et al. | |
| 4,722,336 A | 2/1988 | Kim et al. | |
| 4,723,544 A | 2/1988 | Moore et al. | |
| 4,727,565 A | 2/1988 | Ericson | |
| RE32,619 E | 3/1988 | Damadian | |
| 4,733,969 A | 3/1988 | Case et al. | |
| 4,737,032 A | 4/1988 | Addleman et al. | |
| 4,737,794 A | 4/1988 | Jones | |
| 4,737,921 A | 4/1988 | Goldwasser et al. | |
| 4,742,356 A | 5/1988 | Kuipers | |
| 4,742,815 A | 5/1988 | Ninan et al. | |
| 4,743,770 A | 5/1988 | Lee | |
| 4,743,771 A | 5/1988 | Sacks et al. | |
| 4,745,290 A | 5/1988 | Frankel et al. | |
| 4,750,487 A | 6/1988 | Zanetti | |
| 4,753,528 A | 6/1988 | Hines et al. | |

(56) References Cited

U.S. PATENT DOCUMENTS

| | | |
|---|---|---|
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,787,591 A | 11/1988 | Villacorta |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,679 A | 3/1989 | Shimonaka et al. |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,951,677 A | 8/1990 | Crowley et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 4,994,069 A | 2/1991 | Ritchart et al. |
| 5,002,058 A | 3/1991 | Martinelli |
| 5,005,592 A | 4/1991 | Cartmell |
| 5,007,612 A * | 4/1991 | Manfre ............... A01K 97/00 220/DIG. 9 |
| 5,013,317 A | 5/1991 | Cole et al. |
| 5,016,639 A | 5/1991 | Allen |
| 5,017,139 A | 5/1991 | Mushabac |
| 5,021,888 A | 6/1991 | Kondou et al. |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,186 A | 10/1991 | Yamamoto et al. |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,104,393 A | 4/1992 | Isner et al. |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,171,245 A | 12/1992 | Cezana |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,622 A | 7/1993 | Brossoit |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,301,061 A | 4/1994 | Nakada et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,320,249 A | 6/1994 | Strech |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |

(56) References Cited

U.S. PATENT DOCUMENTS

| | | |
|---|---|---|
| 5,341,807 A | 8/1994 | Nardella |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,380,302 A | 1/1995 | Orth |
| 5,383,454 A | 1/1995 | Bucholz |
| 5,383,852 A | 1/1995 | Stevens-Wright |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,469,847 A | 11/1995 | Zinreich et al. |
| 5,474,075 A | 12/1995 | Goldberg et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,489,256 A | 2/1996 | Adair |
| 5,490,196 A | 2/1996 | Rudich et al. |
| 5,494,034 A | 2/1996 | Schlondorff et al. |
| 5,503,416 A | 4/1996 | Aoki et al. |
| 5,506,102 A | 4/1996 | McDonnell |
| 5,513,637 A | 5/1996 | Twiss et al. |
| 5,514,146 A | 5/1996 | Lam et al. |
| 5,515,160 A | 5/1996 | Schulz et al. |
| 5,515,641 A | 5/1996 | D'Alessandro |
| 5,517,990 A | 5/1996 | Kalfas et al. |
| 5,522,815 A | 6/1996 | Durgin, Jr. et al. |
| 5,531,227 A | 7/1996 | Schneider |
| 5,531,520 A | 7/1996 | Grimson et al. |
| 5,531,686 A | 7/1996 | Lundquist et al. |
| 5,535,973 A | 7/1996 | Bailey et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,555,883 A | 9/1996 | Avitall |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,571,083 A | 11/1996 | Lemelson |
| 5,572,999 A | 11/1996 | Funda et al. |
| 5,573,493 A | 11/1996 | Sauer et al. |
| 5,573,533 A | 11/1996 | Strul |
| 5,575,794 A | 11/1996 | Walus et al. |
| 5,575,798 A | 11/1996 | Koutrouvelis |
| 5,577,991 A | 11/1996 | Akui et al. |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,175 A | 7/1997 | Adair |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,853 A | 2/1998 | Clark et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,728,047 A | 3/1998 | Edoga |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,741,214 A | 4/1998 | Ouchi et al. |
| 5,742,394 A | 4/1998 | Hansen |

(56) References Cited

U.S. PATENT DOCUMENTS

| | | |
|---|---|---|
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,755,725 A | 5/1998 | Druais |
| RE35,816 E | 6/1998 | Schulz |
| 5,758,667 A | 6/1998 | Slettenmark |
| 5,762,064 A | 6/1998 | Polvani |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,782,765 A | 7/1998 | Jonkman |
| 5,787,886 A | 8/1998 | Kelly et al. |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,820,591 A | 10/1998 | Thompson et al. |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |
| 5,836,954 A | 11/1998 | Heilbrun et al. |
| 5,840,024 A | 11/1998 | Taniguchi et al. |
| 5,840,025 A | 11/1998 | Ben-Haim |
| 5,842,984 A | 12/1998 | Avitall |
| 5,843,051 A | 12/1998 | Adams et al. |
| 5,843,076 A | 12/1998 | Webster, Jr. et al. |
| 5,846,183 A | 12/1998 | Chilcoat |
| 5,848,967 A | 12/1998 | Cosman |
| 5,851,183 A | 12/1998 | Bucholz |
| 5,865,726 A | 2/1999 | Katsurada et al. |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,879,499 A | 3/1999 | Corvi |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,893,885 A | 4/1999 | Webster, Jr. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,935,160 A | 8/1999 | Auricchio et al. |
| 5,938,603 A | 8/1999 | Ponzi |
| 5,938,694 A | 8/1999 | Jaraczewski et al. |
| 5,947,925 A | 9/1999 | Ashiya et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,004,269 A | 12/1999 | Crowley et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,035,229 A | 3/2000 | Silverstein et al. |
| 6,050,724 A | 4/2000 | Schmitz et al. |
| 6,059,718 A | 5/2000 | Taniguchi et al. |
| 6,061,588 A | 5/2000 | Thornton et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,086,529 A | 7/2000 | Arndt |
| 6,096,050 A | 8/2000 | Audette |
| 6,104,944 A | 8/2000 | Martinelli |
| 6,112,111 A | 8/2000 | Glantz |
| 6,117,070 A | 9/2000 | Akiba |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,134,003 A | 10/2000 | Tearney et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,171,303 B1 | 1/2001 | Ben-Haim et al. |
| 6,172,499 B1 | 1/2001 | Ashe |
| 6,175,756 B1 | 1/2001 | Ferre et al. |
| 6,178,345 B1 | 1/2001 | Vilsmeier et al. |
| 6,183,444 B1 | 2/2001 | Glines et al. |
| 6,188,355 B1 | 2/2001 | Gilboa |
| 6,192,280 B1 | 2/2001 | Sommer et al. |
| 6,194,639 B1 | 2/2001 | Botella et al. |
| 6,200,262 B1 | 3/2001 | Ouchi |
| 6,201,387 B1 | 3/2001 | Govari |
| 6,203,493 B1 | 3/2001 | Ben-Haim |
| 6,203,497 B1 | 3/2001 | Dekel et al. |
| 6,210,362 B1 | 4/2001 | Ponzi |
| 6,210,378 B1 | 4/2001 | Ouchi |
| 6,211,666 B1 | 4/2001 | Acker |
| 6,213,995 B1 | 4/2001 | Steen et al. |
| 6,216,027 B1 | 4/2001 | Willis et al. |
| 6,223,067 B1 | 4/2001 | Vilsmeier et al. |
| 6,226,543 B1 | 5/2001 | Gilboa et al. |
| 6,233,476 B1 | 5/2001 | Strommer et al. |
| 6,236,875 B1 | 5/2001 | Bucholz et al. |
| 6,246,231 B1 | 6/2001 | Ashe |
| 6,246,784 B1 | 6/2001 | Summers et al. |
| 6,253,770 B1 | 7/2001 | Acker et al. |
| 6,259,942 B1 | 7/2001 | Westermann et al. |

(56) References Cited

U.S. PATENT DOCUMENTS

| | | |
|---|---|---|
| 6,273,896 B1 | 8/2001 | Franck et al. |
| 6,285,902 B1 | 9/2001 | Kienzle, III et al. |
| 6,286,798 B1 | 9/2001 | Chun |
| 6,298,262 B1 | 10/2001 | Franck et al. |
| 6,306,097 B1 | 10/2001 | Park et al. |
| 6,314,310 B1 | 11/2001 | Ben-Haim et al. |
| 6,319,250 B1 | 11/2001 | Falwell et al. |
| 6,332,089 B1 | 12/2001 | Acker et al. |
| 6,335,617 B1 | 1/2002 | Osadchy et al. |
| 6,341,231 B1 | 1/2002 | Ferre et al. |
| 6,343,728 B1 | 2/2002 | Carbone |
| 6,345,112 B1 | 2/2002 | Summers et al. |
| 6,351,659 B1 | 2/2002 | Vilsmeier |
| 6,355,027 B1 | 3/2002 | Le et al. |
| 6,366,799 B1 | 4/2002 | Acker et al. |
| 6,368,316 B1 | 4/2002 | Jansen et al. |
| 6,373,240 B1 | 4/2002 | Govari |
| 6,381,485 B1 | 4/2002 | Hunter et al. |
| 6,381,490 B1 | 4/2002 | Ostrovsky |
| 6,422,994 B1 | 7/2002 | Kaneko et al. |
| 6,423,009 B1 | 7/2002 | Downey et al. |
| 6,424,856 B1 | 7/2002 | Vilsmeier et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,443,894 B1 | 9/2002 | Sumanaweera et al. |
| 6,445,943 B1 | 9/2002 | Ferre et al. |
| 6,447,504 B1 | 9/2002 | Ben-Haim et al. |
| 6,453,190 B1 | 9/2002 | Acker et al. |
| 6,468,265 B1 | 10/2002 | Evans et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 | 11/2002 | Govari |
| 6,485,413 B1 | 11/2002 | Boppart et al. |
| 6,488,674 B2 | 12/2002 | Becker et al. |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,547,722 B1 | 4/2003 | Higuma et al. |
| 6,551,325 B2 | 4/2003 | Neubauer et al. |
| 6,579,277 B1 | 6/2003 | Rabiner et al. |
| 6,580,938 B1 | 6/2003 | Acker |
| 6,584,174 B2 | 6/2003 | Schubert et al. |
| 6,585,639 B1 | 7/2003 | Kotmel et al. |
| 6,591,129 B1 | 7/2003 | Ben-Haim et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,612,485 B2 | 9/2003 | Lackner et al. |
| 6,618,612 B1 | 9/2003 | Acker et al. |
| 6,626,339 B2 | 9/2003 | Gates et al. |
| 6,628,980 B2 | 9/2003 | Atalar et al. |
| 6,631,876 B1 | 10/2003 | Phillips |
| 6,640,128 B2 | 10/2003 | Vilsmeier et al. |
| 6,650,927 B1 | 11/2003 | Keidar |
| 6,666,864 B2 | 12/2003 | Bencini et al. |
| 6,676,659 B2 | 1/2004 | Hutchins et al. |
| 6,690,963 B2 | 2/2004 | Ben-Haim et al. |
| 6,694,162 B2 | 2/2004 | Hartlep |
| 6,701,179 B1 | 3/2004 | Martinelli et al. |
| 6,706,041 B1 | 3/2004 | Costantino |
| 6,711,429 B1 | 3/2004 | Gilboa et al. |
| 6,712,842 B1 | 3/2004 | Gifford, III et al. |
| 6,751,492 B2 | 6/2004 | Ben-Haim |
| 6,770,027 B2 | 8/2004 | Banik et al. |
| 6,788,967 B2 | 9/2004 | Ben-Haim et al. |
| 6,796,963 B2 | 9/2004 | Carpenter et al. |
| 6,887,236 B2 | 5/2005 | Gilboa |
| 6,947,788 B2 | 9/2005 | Gilboa et al. |
| 6,960,161 B2 | 11/2005 | Amling et al. |
| 6,995,729 B2 | 2/2006 | Govari et al. |
| 7,022,066 B2 | 4/2006 | Yokoi et al. |
| 7,101,380 B2 | 9/2006 | Khachin et al. |
| 7,182,756 B2 | 2/2007 | Saeed et al. |
| 7,197,354 B2 | 3/2007 | Sobe |
| 7,233,820 B2 | 6/2007 | Gilboa |
| 7,236,567 B2 | 6/2007 | Sandkamp et al. |
| 7,286,868 B2 | 10/2007 | Govari |
| 7,301,332 B2 | 11/2007 | Govari et al. |
| 7,321,228 B2 | 1/2008 | Govari |
| 7,324,915 B2 | 1/2008 | Altmann et al. |
| 7,343,195 B2 | 3/2008 | Strommer et al. |
| 7,353,125 B2 | 4/2008 | Nieminen et al. |
| 7,357,795 B2 | 4/2008 | Kaji et al. |
| 7,366,562 B2 | 4/2008 | Dukesherer et al. |
| 7,370,656 B2 | 5/2008 | Gleich et al. |
| 7,373,271 B1 | 5/2008 | Schneider |
| 7,386,339 B2 | 6/2008 | Strommer et al. |
| 7,397,364 B2 | 7/2008 | Govari |
| 7,399,296 B2 | 7/2008 | Poole et al. |
| 7,497,029 B2 | 3/2009 | Plassky et al. |
| 7,505,809 B2 | 3/2009 | Strommer et al. |
| 7,536,218 B2 | 5/2009 | Govari et al. |
| RE40,852 E | 7/2009 | Martinelli et al. |
| 7,570,987 B2 | 8/2009 | Raabe et al. |
| 7,577,474 B2 | 8/2009 | Vilsmeier |
| 7,579,837 B2 | 8/2009 | Fath et al. |
| 7,587,235 B2 | 9/2009 | Wist et al. |
| 7,597,296 B2 | 10/2009 | Conway |
| 7,599,535 B2 | 10/2009 | Kiraly et al. |
| 7,599,810 B2 | 10/2009 | Yamazaki |
| 7,630,753 B2 | 12/2009 | Simon et al. |
| 7,634,122 B2 | 12/2009 | Bertram et al. |
| 7,636,595 B2 | 12/2009 | Marquart et al. |
| 7,641,609 B2 | 1/2010 | Ohnishi et al. |
| 7,648,458 B2 | 1/2010 | Niwa et al. |
| 7,652,468 B2 | 1/2010 | Kruger et al. |
| 7,657,300 B2 | 2/2010 | Hunter et al. |
| 7,659,912 B2 | 2/2010 | Akimoto et al. |
| 7,660,623 B2 | 2/2010 | Hunter et al. |
| 7,680,528 B2 | 3/2010 | Pfister et al. |
| 7,684,849 B2 | 3/2010 | Wright et al. |
| 7,686,767 B2 | 3/2010 | Maschke |
| 7,688,064 B2 | 3/2010 | Shalgi et al. |
| 7,696,899 B2 | 4/2010 | Immerz et al. |
| 7,697,972 B2 | 4/2010 | Verard et al. |
| 7,697,973 B2 | 4/2010 | Strommer et al. |
| 7,697,974 B2 | 4/2010 | Jenkins et al. |
| 7,720,517 B2 | 5/2010 | Drysen |
| 7,722,565 B2 | 5/2010 | Wood et al. |
| 7,725,154 B2 | 5/2010 | Beck et al. |
| 7,725,164 B2 | 5/2010 | Suurmond et al. |
| 7,727,269 B2 | 6/2010 | Abraham-Fuchs et al. |
| 7,729,742 B2 | 6/2010 | Govari |
| 7,744,605 B2 | 6/2010 | Vilsmeier et al. |
| 7,747,307 B2 | 6/2010 | Wright et al. |
| 7,751,865 B2 | 7/2010 | Jascob et al. |
| 8,083,432 B2 | 12/2011 | Limpert |
| 8,317,149 B2 * | 11/2012 | Greenburg ......... A61B 1/00128 248/228.7 |
| 8,663,088 B2 | 3/2014 | Greenburg et al. |
| 9,089,261 B2 | 7/2015 | Greenburg et al. |
| 2001/0004676 A1 | 6/2001 | Ouchi |
| 2001/0007918 A1 | 7/2001 | Vilsmeier et al. |
| 2001/0007925 A1 | 7/2001 | Ritchart et al. |
| 2001/0031919 A1 | 10/2001 | Strommer et al. |
| 2001/0034530 A1 | 10/2001 | Malackowski et al. |
| 2001/0036245 A1 | 11/2001 | Kienzle et al. |
| 2002/0026097 A1 | 2/2002 | Akiba |
| 2002/0067408 A1 | 6/2002 | Adair et al. |
| 2002/0087100 A1 | 7/2002 | Onuki et al. |
| 2002/0095081 A1 | 7/2002 | Vilsmeier |
| 2002/0128565 A1 | 9/2002 | Rudy |
| 2002/0137014 A1 | 9/2002 | Anderson et al. |
| 2002/0162555 A1 | 11/2002 | West et al. |
| 2002/0165503 A1 | 11/2002 | Morris et al. |
| 2002/0173689 A1 | 11/2002 | Kaplan |
| 2002/0193686 A1 | 12/2002 | Gilboa |

(56) References Cited

U.S. PATENT DOCUMENTS

| | | |
|---|---|---|
| 2003/0018251 A1 | 1/2003 | Solomon |
| 2003/0028096 A1 | 2/2003 | Niwa et al. |
| 2003/0040657 A1 | 2/2003 | Yamaya et al. |
| 2003/0074011 A1 | 4/2003 | Gilboa et al. |
| 2003/0086599 A1 | 5/2003 | Armato et al. |
| 2003/0114742 A1 | 6/2003 | Lewkowicz et al. |
| 2003/0142753 A1 | 7/2003 | Gunday |
| 2003/0160721 A1 | 8/2003 | Gilboa et al. |
| 2003/0171653 A1 | 9/2003 | Yokoi et al. |
| 2003/0227547 A1 | 12/2003 | Iddan |
| 2004/0015049 A1 | 1/2004 | Zaar |
| 2004/0024309 A1 | 2/2004 | Ferre et al. |
| 2004/0086161 A1 | 5/2004 | Sivaramakrishna et al. |
| 2004/0097804 A1 | 5/2004 | Sobe |
| 2004/0138548 A1 | 7/2004 | Strommer et al. |
| 2004/0169509 A1 | 9/2004 | Czipott et al. |
| 2004/0249267 A1 | 12/2004 | Gilboa |
| 2004/0260201 A1 | 12/2004 | Mueller |
| 2005/0011786 A1 | 1/2005 | Wood et al. |
| 2005/0033149 A1 | 2/2005 | Strommer et al. |
| 2005/0059890 A1 | 3/2005 | Deal et al. |
| 2005/0080342 A1 | 4/2005 | Gilreath et al. |
| 2005/0085715 A1 | 4/2005 | Dukesherer et al. |
| 2005/0090818 A1 | 4/2005 | Pike et al. |
| 2005/0107688 A1 | 5/2005 | Strommer |
| 2005/0119527 A1 | 6/2005 | Banik et al. |
| 2005/0182292 A1 | 8/2005 | Suzuki |
| 2005/0182295 A1 | 8/2005 | Soper et al. |
| 2005/0197566 A1 | 9/2005 | Strommer et al. |
| 2005/0229934 A1 | 10/2005 | Willeford |
| 2006/0015126 A1 | 1/2006 | Sher |
| 2006/0058647 A1 | 3/2006 | Strommer et al. |
| 2006/0064006 A1 | 3/2006 | Strommer et al. |
| 2006/0069313 A1 | 3/2006 | Couvillon et al. |
| 2006/0149134 A1 | 7/2006 | Soper et al. |
| 2006/0184016 A1 | 8/2006 | Glossop |
| 2007/0163597 A1 | 7/2007 | Mikkaichi et al. |
| 2007/0167714 A1 | 7/2007 | Kiraly et al. |
| 2007/0167738 A1 | 7/2007 | Timinger et al. |
| 2007/0167743 A1 | 7/2007 | Honda et al. |
| 2007/0167806 A1 | 7/2007 | Wood et al. |
| 2007/0225559 A1 | 9/2007 | Clerc et al. |
| 2007/0265639 A1 | 11/2007 | Danek et al. |
| 2007/0276180 A1 | 11/2007 | Greenburg et al. |
| 2007/0287901 A1 | 12/2007 | Strommer et al. |
| 2007/0293721 A1 | 12/2007 | Gilboa |
| 2008/0086051 A1 | 4/2008 | Voegele |
| 2008/0097187 A1 | 4/2008 | Gielen et al. |
| 2008/0118135 A1 | 5/2008 | Averbuch et al. |
| 2008/0125760 A1 | 5/2008 | Gilboa |
| 2008/0132757 A1 | 6/2008 | Tgavalekos |
| 2008/0132909 A1 | 6/2008 | Jascob et al. |
| 2008/0132911 A1 | 6/2008 | Sobe |
| 2008/0139886 A1 | 6/2008 | Tatsuyama |
| 2008/0139915 A1 | 6/2008 | Dolan et al. |
| 2008/0144909 A1 | 6/2008 | Wiemker et al. |
| 2008/0147000 A1 | 6/2008 | Seibel et al. |
| 2008/0154172 A1 | 6/2008 | Mauch |
| 2008/0157755 A1 | 7/2008 | Kruger et al. |
| 2008/0161682 A1 | 7/2008 | Kendrick et al. |
| 2008/0162074 A1 | 7/2008 | Schneider |
| 2008/0183071 A1 | 7/2008 | Strommer et al. |
| 2008/0188749 A1 | 8/2008 | Rasche et al. |
| 2009/0182224 A1 | 7/2009 | Shmarak et al. |
| 2009/0234223 A1 | 9/2009 | Onoda et al. |
| 2009/0318797 A1 | 12/2009 | Hadani |
| 2010/0016757 A1 | 1/2010 | Greenburg et al. |

FOREIGN PATENT DOCUMENTS

| | | |
|---|---|---|
| DE | 3508730 A1 | 9/1986 |
| DE | 3520782 A1 | 12/1986 |
| DE | 3717871 A1 | 12/1988 |
| DE | 3831278 A1 | 3/1989 |
| DE | 3838011 A1 | 7/1989 |
| DE | 4213426 A1 | 10/1992 |
| DE | 4225112 C1 | 12/1993 |
| DE | 4233978 C1 | 4/1994 |
| DE | 19610984 A1 | 9/1997 |
| DE | 19715202 A1 | 10/1998 |
| DE | 19751761 A1 | 10/1998 |
| DE | 19832296 A1 | 2/1999 |
| DE | 19747427 A1 | 5/1999 |
| DE | 10085137 T1 | 11/2002 |
| EP | 0062941 A1 | 10/1982 |
| EP | 0119660 A1 | 9/1984 |
| EP | 0155857 A2 | 9/1985 |
| EP | 0319844 A1 | 6/1989 |
| EP | 0326768 A2 | 8/1989 |
| EP | 0350996 A1 | 1/1990 |
| EP | 0419729 A1 | 4/1991 |
| EP | 0427358 A1 | 5/1991 |
| EP | 0456103 A2 | 11/1991 |
| EP | 0581704 A1 | 2/1994 |
| EP | 0600610 A2 | 6/1994 |
| EP | 0651968 A1 | 5/1995 |
| EP | 0655138 A1 | 5/1995 |
| EP | 0796633 A1 | 9/1997 |
| EP | 0857461 A2 | 8/1998 |
| EP | 0894473 A2 | 2/1999 |
| EP | 0908146 A2 | 4/1999 |
| EP | 0930046 A2 | 7/1999 |
| EP | 1078644 A1 | 2/2001 |
| EP | 1255113 A1 | 11/2002 |
| EP | 1543765 A1 | 6/2005 |
| EP | 1667749 A2 | 6/2006 |
| EP | 2096523 A1 | 9/2009 |
| FR | 2417970 A1 | 9/1979 |
| FR | 2618211 A1 | 1/1989 |
| GB | 2094590 A | 9/1982 |
| GB | 2164856 A | 4/1986 |
| JP | 63-240851 A | 10/1988 |
| JP | 03-267054 A | 11/1991 |
| JP | 06-125869 A | 5/1994 |
| JP | 06194639 A | 7/1994 |
| JP | 07-043619 A | 2/1995 |
| JP | 09-253038 A | 9/1997 |
| JP | 10-197807 A | 7/1998 |
| JP | 2000-075218 A | 3/2000 |
| JP | 2000-279379 A | 10/2000 |
| JP | 2000316986 A | 11/2000 |
| JP | 2001-231743 A | 8/2001 |
| JP | 2001-275942 A | 10/2001 |
| WO | 88/09151 A1 | 12/1988 |
| WO | 89/05123 A1 | 6/1989 |
| WO | 90/05494 A1 | 5/1990 |
| WO | 91/03982 A1 | 4/1991 |
| WO | 91/04711 A1 | 4/1991 |
| WO | 91/07726 A1 | 5/1991 |
| WO | 92/03090 A1 | 3/1992 |
| WO | 92/06645 A1 | 4/1992 |
| WO | 94/04938 A1 | 3/1994 |
| WO | 94/23647 A1 | 10/1994 |
| WO | 94/24933 A1 | 11/1994 |
| WO | 95/07055 A1 | 3/1995 |
| WO | 96/11624 A2 | 4/1996 |
| WO | 96/32059 A1 | 10/1996 |
| WO | 97/29682 A1 | 8/1997 |
| WO | 97/29684 A1 | 8/1997 |
| WO | 97/36192 A1 | 10/1997 |
| WO | 97/49453 A1 | 12/1997 |
| WO | 98/08554 A1 | 3/1998 |
| WO | 98/38908 A1 | 9/1998 |
| WO | 99/15097 A2 | 4/1999 |
| WO | 99/21498 A1 | 5/1999 |
| WO | 99/23956 A1 | 5/1999 |
| WO | 99/26549 A1 | 6/1999 |
| WO | 99/27839 A2 | 6/1999 |
| WO | 99/29253 A1 | 6/1999 |
| WO | 99/33406 A1 | 7/1999 |
| WO | 99/37208 A1 | 7/1999 |
| WO | 99/38449 A1 | 8/1999 |
| WO | 99/52094 A1 | 10/1999 |
| WO | 99/60939 A1 | 12/1999 |

(56) References Cited

FOREIGN PATENT DOCUMENTS

| WO | 00/06701 | A1 | 2/2000 |
|---|---|---|---|
| WO | 00/14056 | A1 | 3/2000 |
| WO | 00/16684 | A1 | 3/2000 |
| WO | 00/35531 | A1 | 6/2000 |
| WO | 01/19235 | A1 | 3/2001 |
| WO | 01/30437 | A1 | 5/2001 |
| WO | 01/67035 | A1 | 9/2001 |
| WO | 01/87136 | A2 | 11/2001 |
| WO | 01/87398 | A2 | 11/2001 |
| WO | 01/91842 | A1 | 12/2001 |
| WO | 02/24054 | A2 | 3/2002 |
| WO | 02/064011 | A2 | 8/2002 |
| WO | 02/070047 | A1 | 9/2002 |
| WO | 03/086498 | A2 | 10/2003 |
| WO | 2004/023986 | A1 | 3/2004 |
| WO | 2005025635 | A2 | 3/2005 |
| WO | 2005074380 | A2 | 8/2005 |
| WO | 20061116597 | | 11/2006 |
| WO | 2007109418 | A2 | 9/2007 |

OTHER PUBLICATIONS

United States Patent and Trademark Office, Notice of Allowance dated Jan. 3, 2005 in U.S. Appl. No. 10/137,415, 9 pages.
Shmarak, I. et al., U.S. Appl. No. 10/986,567, filed Nov. 2004 (abandoned, unpublished), 84 pages.
United States Patent and Trademark Office, Office Action dated Jul. 1, 2004 in U.S. Appl. No. 10/10,137,415, 14 pages.
WIPO, U.S. International Preliminary Examining Authority, International Preliminary Report on Patentability dated Jan. 24, 2004 in International Patent Application No. PCT/IL2003/000323, 3 pages.
WIPO, U.S. International Search Authority, International Search Report dated Dec. 8, 2003 in International Patent Application No. PCT/IL2003/000323, 1 page.
Stenoien, D.L. et al., "Ligand-Mediated Assembly and Real-Time Cellular Dynamics of Estrogen Receptor .alpha.-Coactivator Complexes in Living Cells," Molecular and Cellular Biology, Jul. 2001, pp. 4404-4412, 9 pages.
McKenna, N.J. et al., "Nuclear Receptor Coregulators: Cellular and Molecular Biology," Endocrine Reviews 20(3): 321-344, Jun. 1, 1999, 24 pages.
Ding, X.F. et al., "Nuclear Receptor-Binding Sites of Coactivators Glucocorticoid Receptor Interacting Protein 1 (GRIP1) and Steroid Receptor Coactivator 1 (SRC-1): Multiple Motifs with Different Binding Specificities," MolecularEndocrinology12:302-313, Feb. 1, 1998 (9 pages).
European Patent Office, Supplementary European Search Report dated Sep. 18, 2008, 4 pages.
United States Patent and Trademark Office, Final Office Action dated May 1, 2012 in U.S. Appl. No. 12/476,976, 6 pages.
European Patent Office, Decision to Grant dated Apr. 13, 2012 in European Patent Application No. 10191689, 1 page.
United States Patent and Trademark Office, Office Action dated Feb. 22, 2012 in U.S. Appl. No. 12/233,933, 10 pages.
European Patent Office, Extended European Search Report dated Feb. 20, 2012 in European Patent Application No. 06701745, 9 pages.
United States Patent and Trademark Office, Final Office Action dated Dec. 19, 2011 in U.S. Appl. No. 10/571,793, 8 pages.
European Patent Office, Extended European Search Report dated Nov. 22, 2011 in European Patent Application No. 11182823, 5 pages.
European Patent Office, Extended European Search Report dated Nov. 21, 2011 in European Patent Application No. 11182823, 5 pages.
United States Patent and Trademark Office, Office Action dated Nov. 18, 2011 in U.S. Appl. No. 12/476,976, 8 pages.
WIPO, U.S. International Search Authority, International Search Report and Written Opinion dated Oct. 7, 2011 in International Patent Application No. PCT/US2011/040579, 8 pages.
European Patent Office, Extended European Search Report dated Sep. 6, 2011 in European Patent Application No. 03719056, 6 pages.
European Patent Office, Extended European Search Report dated Sep. 6, 2011 in European Patent Application No. 11174666, 6 pages.
Japanese Patent Office, Official Action dated Aug. 23, 2011 in Japanese Patent Application No. 2007-552806, 7 pages.
Japanese Patent Office, Examiner's Report dated Aug. 19, 2011 in Japanese Patent Application No. JP2007-552806, 7 pages.
WIPO, U.S. International Preliminary Examining Authority, International Preliminary Report on Patentability dated Jun. 30, 2011 in International Patent Application No. PCT/US2009/069073, 6 pages.
United States Patent and Trademark Office, Office Action dated May 24, 2011 in U.S. Appl. No. 10/571,793, 8 pages.
United States Patent and Trademark Office, Office Action dated Mar. 31, 2011 in U.S. Appl. No. 12/643,917, 10 pages.
European Patent Office, Extended European Search Report dated Mar. 8, 2011 in European Patent Application No. 10191689, 4 pages.
United States Patent and Trademark Office, Office Action dated Dec. 23, 2010 in U.S. Appl. No. 10/571,793, 11 pages.
European Patent Office, Supplementary European Search Report dated Nov. 15, 2010 in European Patent Application No. EP10159373.9, 12 pages.
United States Patent and Trademark Office, Office Action dated Oct. 4, 2010 in U.S. Appl. No. 12/271,175, 11 pages.
European Patent Office, Examination Report dated Sep. 11, 2010 in European Patent Application No. 3719056, 4 pages.
United States Patent and Trademark Office, Final Office Action dated Jun. 23, 2010 in U.S. Appl. No. 10/571,793, 10 pages.
WIPO, U.S. International Search Authority, International Search Report and Written Opinion dated Apr. 23, 2010 in International Patent Application No. PCT/US2009/069073, 8 pages.
WIPO, U.S. International Preliminary Examining Authority, International Preliminary Report on Patentability dated Apr. 8, 2010 in International Patent Application No. PCT/IB2008/002543, 7 pages.
European Patent Office, Examination Report dated Mar. 30, 2010 in European Patent Application No. EP05737664.2, 5 pages.
Japanese Patent Office, Official Action dated Mar. 12, 2010 in Japanese Patent Application No. 2006-526007, 5 pages.
European Patent Office, Extended European Search Report dated Dec. 1, 2009 in European Patent Application No. 09157586, 7 pages.
United States Patent and Trademark Office, Office Action dated Nov. 27, 2009 in U.S. Appl. No. 10/571,793, 11 pages.
WIPO, U.S. International Search Authority, International Search Report and Written Opinion dated Nov. 12, 2009 in International Patent Application No. PCT/IL2009/000697, 9 pages.
WIPO, U.S. International Search Authority, International Search Report and Written Opinion dated Sep. 22, 2009 in International Patent Application No. PCT/IL2009/000553, 7 pages.
WIPO, U.S. International Preliminary Examining Authority, International Preliminary Report on Patentability dated Jul. 28, 2009 in International Patent Application No. PCT/IL2005/000159, 6 pages.
European Patent Office, Examination Report dated Jul. 14, 2009 in European Patent Application No. 03719056, 6 pages.
United States Patent and Trademark Office, Office Action dated Jun. 24, 2009 in U.S. Appl. No. 10/571,695, 11 pages.
WIPO, U.S. International Preliminary Examining Authority, International Preliminary Report on Patentability dated Mar. 30, 2009 in International Patent Application No. PCT/IL2006/000113, 6 pages.
WIPO, U.S. International Search Authority, International Search Report and Written Opinion dated Mar. 16, 2009 in International Patent Application No. PCT/IB2008/002543, 9 pages.
United States Patent and Trademark Office, Final Office Action dated Mar. 12, 2009 in U.S. Appl. No. 10/597,747, 7 pages.
European Patent Office, Supplementary European Search Report dated Feb. 27, 2009 in European Patent Application No. 03719056, 6 pages.
European Patent Office, Decision to Grant dated Feb. 20, 2009 in European Patent Application No. 04770514, 24 pages.
WIPO, U.S. International Search Authority, International Search Report and Written Opinion dated Dec. 15, 2008 in International Patent Application No. PCT/IL2006/000113, 6 pages.

(56) References Cited

OTHER PUBLICATIONS

Japanese Patent Office, Official Action dated Dec. 12, 2008 in Japanese Patent Application No. 2008-583508, 9 pages.
European Patent Office, Supplementary European Search Report dated Oct. 7, 2008 in European Patent Application No. 04770514, 4 pages.
United States Patent and Trademark Office, Office Action dated Sep. 11, 2008 in U.S. Appl. No. 10/597,747, 9 pages.
WIPO, U.S. International Search Authority, International Search Report and Written Opinion dated Jul. 11, 2008 in International Patent Application No. PCT-IL2005/000159, 12 pages.
WIPO, U.S. International Preliminary Examining Authority, International Preliminary Report on Patentability dated Oct. 9, 2007 in International Patent Application No. PCT/IL2004/000843, 4 pages.
WIPO, U.S. International Search Authority, International Search Report and Written Opinion dated Sep. 24, 2007 in International Patent Application No. PCT/IL2004/000843, 4 pages.
WIPO, U.S. International Search Authority, International Search Report and Written Opinion dated Jul. 11, 2007 in International Patent Application No. PCT/IL2005/000159, 6 pages.
United States Patent and Trademark Office, Notice of Allowance dated Oct. 6, 2006 in U.S. Appl. No. 10/491,099, 7 pages.
China Patent and Trademark Office, Office Action dated Jun. 19, 2006 in Chinese Patent Application No. 038135485, 5 pages.
United States Patent and Trademark Office, Office Action dated Dec. 30, 2005 in U.S. Appl. No. 10/491,099, 15 pages.

* cited by examiner

SYSTEM OF ACCESSORIES FOR USE WITH BRONCHOSCOPES

CROSS-REFERENCE TO RELATED APPLICATIONS

This application is a continuation of U.S. patent application Ser. No. 10/571,793, filed on Feb. 15, 2007, which is a national stage application of International Application No. PCT/IL04/00843, filed on Sep. 14, 2004, which claims the benefit of and priority to U.S. Provisional Patent Application Ser. Nos. 60/564,944, filed Apr. 26, 2004, 60/550,346 filed Mar. 8, 2004, and 60/502,615 filed Sep. 15, 2003; the contents of each of these incorporated by reference herein in their entirety for all purposes.

FIELD AND BACKGROUND OF THE INVENTION

The present invention relates to bronchoscopy and, in particular, it concerns a system of accessories for use when performing surgical procedures using a bronchoscope.

The most common interventional procedure in the field of Pulmonary Medicine (i.e., medicine pertaining to the respiratory system) is bronchoscopy, in which a bronchoscope is inserted into the airways through the patient's nose or mouth. The instrument consists of a long, thin, flexible tube that typically contains three elements, an illumination arrangement for illuminating the region distal to the bronchoscope's tip via an optical fiber connected to an external light source, an imaging arrangement for delivering back a video image from the bronchoscope's distal tip, and a 'working channel' through which instruments of both diagnostic (e.g., biopsy tools) and therapeutic (e.g., laser, cryo or RF tissue elimination probes) nature are inserted. The distal tip of the bronchoscope is steerable; rotating a lever placed at the handle of the bronchoscope actuates the steering mechanism by deflection the tip in two opposite directions.

Bronchoscopies are applied routinely to the diagnosis and treatment of diseases such as Lung Cancer, Airway Stenosis, and Emphysema. They are performed by an expert pulmonologist, also known as a bronchoscopist.

Bronchoscopies are performed by a staff of at least two persons, the bronchoscopist and at least one assistant, usually a nurse. During a typical procedure, the bronchoscopist holds the bronchoscope handle with one hand and the bronchoscope tube with the other hand. He or she manipulates the distal tip of the bronchoscope inside the lung by rotating the deflection lever and by pushing and pulling the tube. Once the tip is brought to the target, a medical diagnosis is achieved and/or treatment is applied by insertion of a bronchoscopic tool into the working channel and out through the distal tip of the bronchoscope tube and performing the diagnosis or treatment.

During insertion and operation the bronchoscopic tool, the distal tip of the bronchoscope should be held steady at the target. Performing all of these tasks concurrently often requires three or four hands, two for securing the bronchoscope in place, and one to two more hands for inserting and actuating the bronchoscopic tool. The complexity of such multi-person operation, requiring delicate coordination between the physician and the assistant, often detracts from the resulting precision of the medical procedure, and the need for additional helping hands often increases its cost.

Of particular relevance to the present invention is a device and method described in PCT patent application publication no. WO 03/086498 entitled "Endoscope Structure and Techniques for Navigation in Brunched Structure" to Gilboa, which is hereby incorporated fully by reference. This patent application describes a method and apparatus in which a locatable guide ("LG"), enveloped by a sheath, is used to navigate a bronchoscopic tool to a location within the lung. The guide/sheath combination is inserted into the lung via the working channel of a bronchoscope. Once the tip of the guide is located at its target, a lock, which is placed at the orifice ("connection port") of the bronchoscope's working channel, is operated to prevent the sheath from sliding in or out of the bronchoscope. The guide is then withdrawn from the sheath, leaving the sheath in place to guide a tool to the required target location.

On the other hand, when the same bronchoscope is used in its primary function for investigation of the bronchi, the same working channel is used to clean disturbing mucus from the airways, using a vacuum pump connected to special connector separate from the orifice of the working channel. For the suction to work properly, the orifice of the working channel should be sealed during application of the suction.

It follows that, during the procedure, the physician typically needs to interchange two different devices to the connection port of the bronchoscope working channel, a seal and a lock, and these must be interchanged depending upon which function the bronchoscope is currently performing.

During the switch between locatable guide and other tools, it is necessary to insert the guide or tool into the free proximal end of the sheath. This step has been found to be somewhat "fiddly" and difficult to achieve quickly due to the flexibility and consequent mechanical instability of the end of the sheath. The problem can be addressed easily by holding the end of the sheath in one hand and the tool in another, but this would again require additional free hands during performance of the procedure.

In order to facilitate operation of a system such as described in the aforementioned application by a single practitioner, it would be preferable to allow the practitioner to temporarily release his or her grip on a secondary tool or device used via the working channel of the bronchoscope. At the same time, it is preferable that the device remains immediately accessible and operable, and does not hang loosely.

There is therefore a need for accessories for use with a bronchoscope which would facilitate operation of a bronchoscope and associated tools by a single practitioner. It would also be advantageous to provide an adapter for the connection port of the working channel of a bronchoscope which would perform both the sealing and tool-locking functions without requiring replacement of an attachment during the procedure. It would further be advantageous to provide an arrangement according to the teachings of the aforementioned PCT patent publication which would facilitate insertion of tools into the guide sheath.

SUMMARY OF THE INVENTION

The present invention relates to various accessories for use when performing surgical procedures using a bronchoscope.

According to the teachings of the present invention there is provided, a sealing and locking adapter for attachment to an access port of a working channel of a bronchoscope to allow insertion and locking of a tool while sealing the access port when not in use, the adapter comprising: (a) a housing configured for mating with the access port of the working channel of the bronchoscope; (b) an attachment configuration associated with the housing and configured for attaching the housing to the access port of the working channel; (c) a sealing arrangement deployed within the housing, the sealing arrangement including an elastomeric valve elastically biased to a normally-closed state wherein the elastomeric valve forms part of a sealing arrangement for resisting passage of air through the access port of the working channel, the elastomeric valve being configured to allow insertion of the tool through the valve and into the working channel; and (d) a clamping arrangement deployed within the housing, the clamping arrangement including an elastomeric clamping block and a tightening mechanism, the tightening mechanism being manually operable to deform the elastomeric clamping block so as to lock in position the tool inserted through the housing and into the working channel.

According to a further feature of the present invention, the elastomeric clamping block is formed as a substantially cylindrical collar with a central clamping bore for passage of the tool.

According to a further feature of the present invention, the central clamping bore features at least one inwardly projecting ridge.

According to a further feature of the present invention, the substantially cylindrical collar has at least one conical surface portion, the tightening mechanism including an axially displaceable element deployed for engaging the at least one conical surface so as to apply an inward locking pressure on the central clamping bore.

According to a further feature of the present invention, the elastomeric valve and the elastomeric clamping block are implemented as a unitary elastomeric insert deployed within the housing.

According to a further feature of the present invention, the elastomeric valve is implemented as an elastomeric membrane cut along a slit.

There is also provided according to the teachings of the present invention, a clip for temporarily retaining a substantially cylindrical body portion of an accessory in predefined relation to a handle of a bronchoscope, the clip comprising: (a) an outer bracket configured for circumscribing at least 180° around the handle of the bronchoscope; (b) a flexible clamping portion deployed within the outer bracket and circumscribing at least 180° around the handle of the bronchoscope; (c) a tightening mechanism associated with the outer bracket and configured to flex at least part of the flexible clamping portion inwards relative to the outer bracket so as to clamp the clip onto the handle of the bronchoscope; and (d) a pair of resilient jaws interconnected with at least one of the outer bracket and the flexible clamping portion, the pair of resilient jaws being configured for gripping an accessory.

According to a further feature of the present invention, there is also provided a resilient insert deployed within the clamping portion.

According to a further feature of the present invention, the pair of resilient jaws is integrally formed with the flexible clamping portion.

According to a further feature of the present invention, the pair of resilient jaws is configured to grip the substantially cylindrical body portion of the accessory substantially perpendicular to a direction of elongation of the bronchoscope handle.

According to a further feature of the present invention, the flexible clamping portion circumscribes at least about 200° around the handle of the bronchoscope.

According to a further feature of the present invention, the flexible clamping portion circumscribes no more than about 250° around the handle of the bronchoscope.

There is also provided according to the teachings of the present invention, a wrap-around handle extension for use with a bronchoscope handle, the wrap-around handle extension comprising: (a) a flexible wrap-around layer provided with complementary fastening arrangements deployed so as to form a conical sleeve for holding the bronchoscope handle; and (b) a hand loop associated with the flexible wrap-around layer and configured for receiving the hand of a user to allow suspension of the conical sleeve from the hand of the user.

According to a further feature of the present invention, the complementary fastening arrangements are implemented as complementary regions of a Velcro fastening arrangement.

According to a further feature of the present invention, there is also provided an accessory suspension strap associated with the flexible wrap-around layer and configured for suspending an accessory from the conical sleeve.

According to a further feature of the present invention, the accessory suspension strap is configured with a releasable fastening configuration to form a releasable suspension loop.

There is also provided according to the teachings of the present invention, a sheath for deployment via a working channel of a bronchoscope for directing a tool to a previously identified position, the sheath comprising: (a) a primary sheath portion extending along a major portion of a length of the sheath, the primary sheath portion having a first degree of flexibility; and (b) a reduced flexibility proximal sheath portion, the proximal sheath portion and the primary sheath portion together defining a contiguous inner lumen, the proximal sheath portion having a lower degree of flexibility than the primary sheath portion.

According to a further feature of the present invention, the primary sheath portion is implemented as a tube formed from a first material, and wherein the proximal sheath portion is implemented as a continuation of the tube formed from the first material circumscribed by a reinforcing sleeve of a second material.

According to a further feature of the present invention, there is also provided a distal sheath portion forming a contiguous inner lumen with the primary sheath portion, the distal sheath portion having a higher degree of flexibility than the primary sheath portion.

According to a further feature of the present invention, there is also provided a proximal end piece mechanically associated with a proximal end of the proximal sheath portion, the proximal end piece defining a conical insertion guide for guiding a tool into the inner lumen.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention relates to various accessories for use when performing surgical procedures using a bronchoscope.

The principles and operation of bronchoscope accessories according to the present invention may be better understood with reference to the drawings and the accompanying description.

By way of introduction, it should be noted that the present invention includes a number of different aspects, each of which is believed to be of patentable significance in its own right. Specifically, with reference to FIGS. 1-4, a sealing and locking adapter will be described. Then, with reference to FIG. 5, a preferred sheath structure will be described. Then, with reference to FIGS. 6-9, a clip structure for retaining an accessory tool will be described. Finally, with reference to FIGS. 10-13, a wrap-around handle extension arrangement will be described.

Figure 3A:
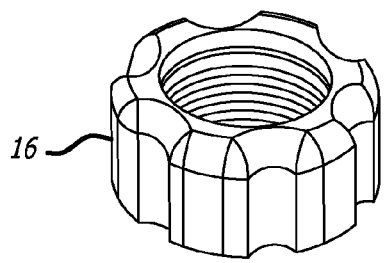
FIG. 3A is an exploded isometric view illustrating the components of the adapter of FIG. 1.
Figure 3A:
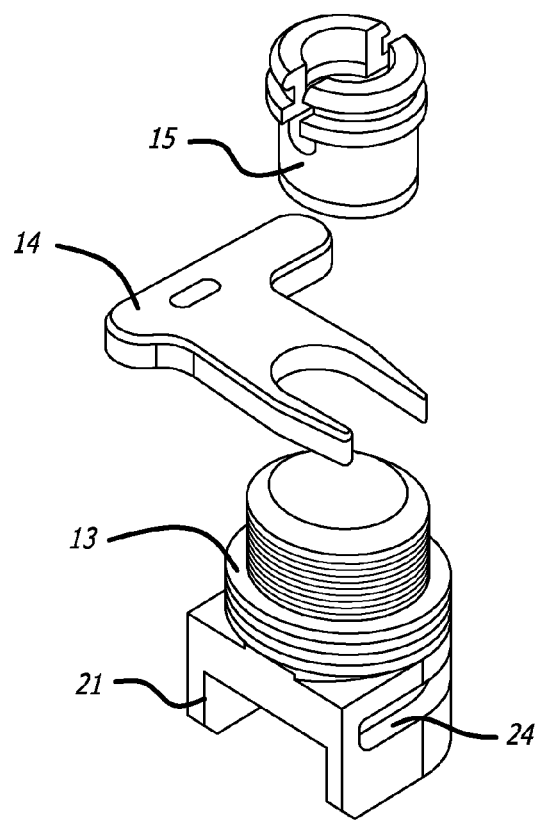
Figure 3A:
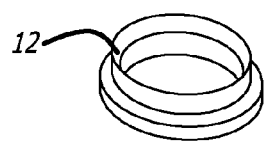
Figure 3A:
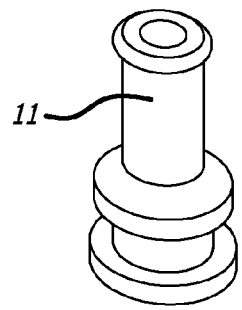
Figure 3B:
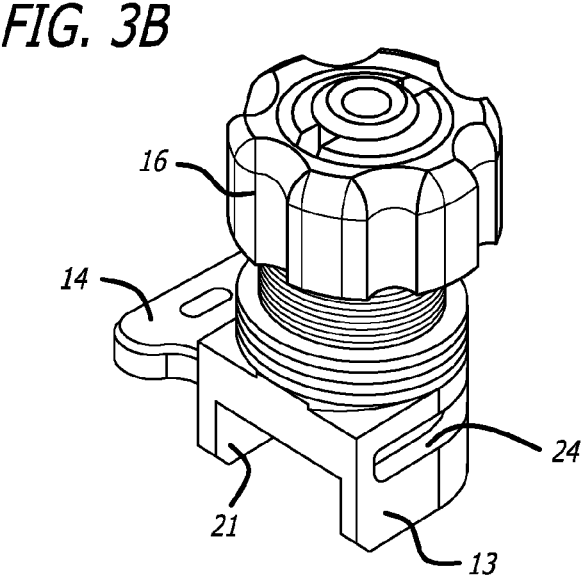
FIG. 3B is an isometric view of the adapter of FIG. 1 when assembled.
Figure 4:
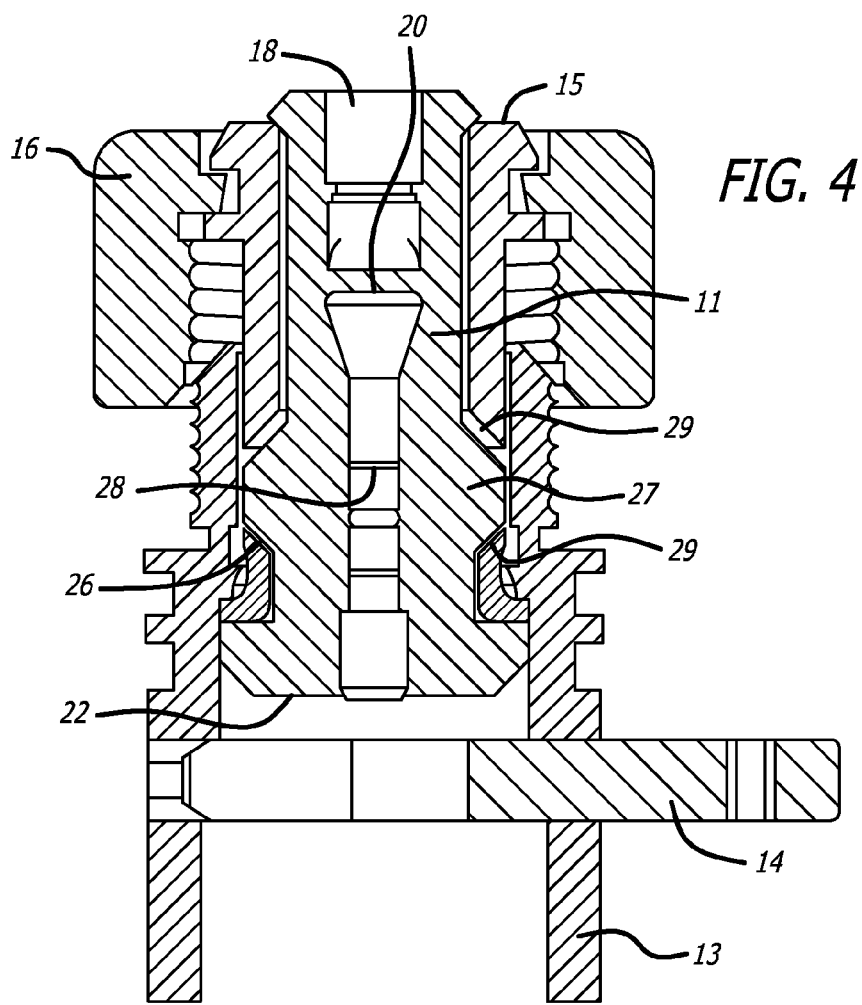
FIG. 4 is an axial cross-sectional view taken through the adapter of FIG. 1.

Referring now to the drawings, FIG. 1-4 illustrate a first aspect of the present invention, namely, a sealing and locking adapter 200 for attachment to an access port ("interface") 110 of a working channel 130 of a bronchoscope 100 to allow insertion and locking of a tool (not shown) while sealing the access port 110 when not in use. Generally speaking, as best seen in FIG. 4, adapter 200 includes a housing 13 configured for mating with the access port 110 and an attachment configuration associated with housing 13 and configured for attaching housing 13 to access port 110 of working channel 130. Adapter 200 includes a sealing arrangement, deployed within housing 13, including an elastomeric valve 20 elastically biased to a normally-closed state (FIG. 4) wherein elastomeric valve 20 forms part of a sealing arrangement for resisting passage of air through the access port 110 of working channel 130. Elastomeric valve 20 is also configured to allow insertion of a tool (not shown) through the valve and into the working channel. Also deployed within housing 13 is a clamping arrangement including an elastomeric clamping block 11 and a tightening mechanism manually operable to deform elastomeric clamping block 11 so as to lock in position a tool inserted through housing 13 and into the working channel 130.

At this stage, it will be immediately clear that adapter 200 provides major advantages over the prior art. Specifically, by providing both a sealing arrangement and a locking configuration within a single adapter, the aforementioned problem of needing to replace the attachments during performance of different parts of a surgical procedure. This and other advantages of this aspect of the present invention will become clearer from the detailed description below.

Figure 1:
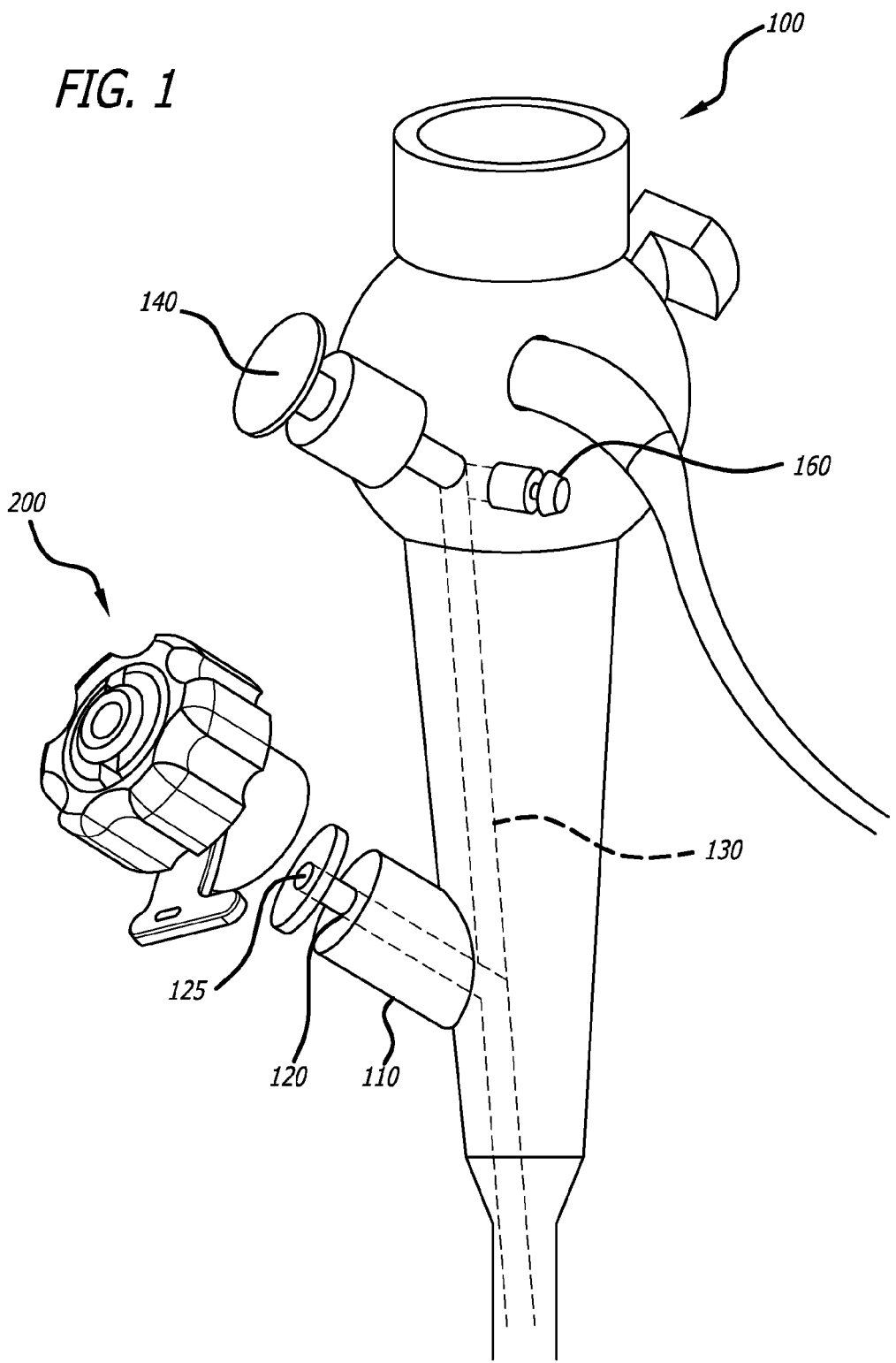
FIG. 1 is a schematic isometric view of part of the handle of a bronchoscope showing a working channel fitted with a sealing and locking adapter, constructed and operative according to the teachings of the present invention.

Referring now specifically to FIG. 1, this shows a schematic drawing of the handle 100 of a bronchoscope. A working channel 130 is included inside handle 100. Tools are inserted into the working channel through an input orifice 125. The working channel is incorporated inside the entire length of the bronchoscope all the way up to its proximal end. In addition, the working channel is also connected to a vacuum pump (not shown) or other source of suction through a valve 140 and through a second connector 160. When the valve is pressed open, the pump sucks the content of the working channel. For the suction to work properly, the working channel should be kept sealed. A gasket fitting 120 is incorporated at the entrance of the working channel on which a rubber gasket can be attached for sealing the orifice (not shown).

Figure 2A:
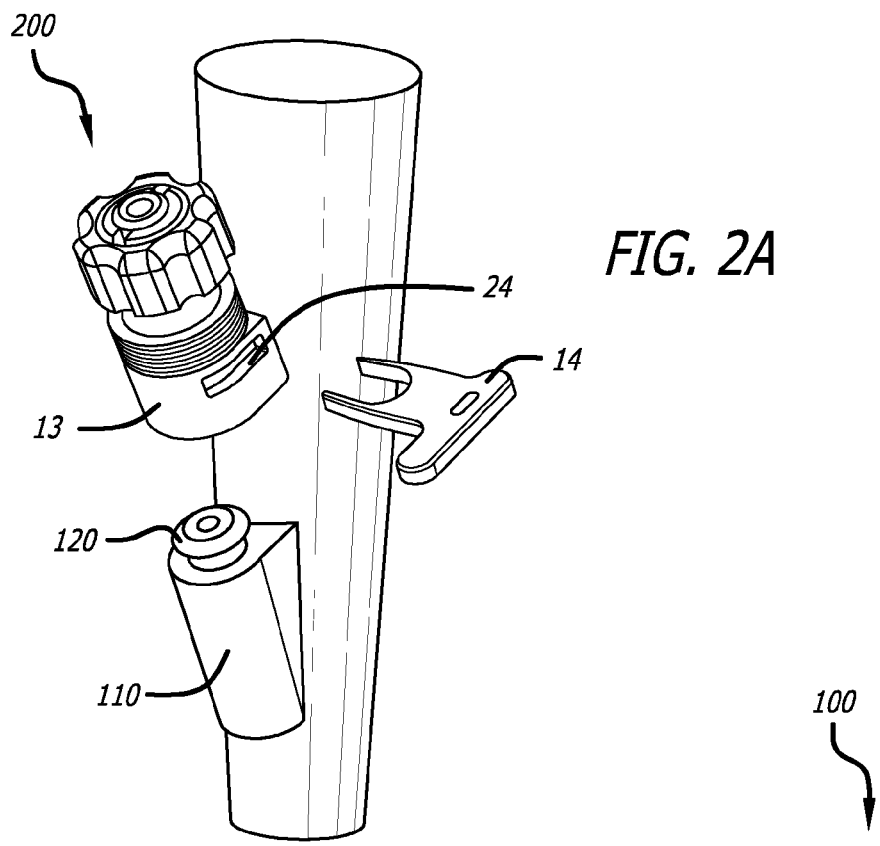
FIG. 2A is an enlarged schematic isometric view showing the adapter of FIG. 1 prior to attachment to the bronchoscope's handle.
Figure 2B:
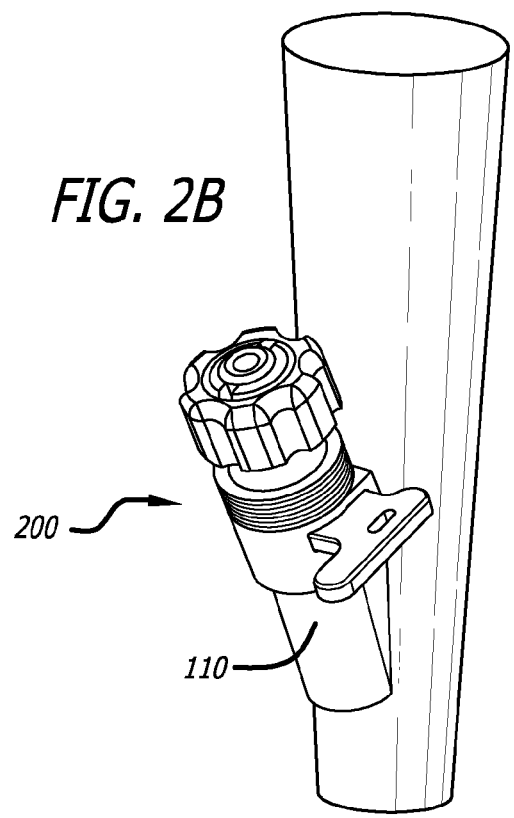
FIG. 2B is an enlarged schematic isometric view showing the adapter of FIG. 1 attached to the bronchoscope's handle.

In a preferred embodiment, adapter 200 is mounted on the working channel interface 110 by connection to the gasket fitting 120. FIGS. 2A and 2B show a preferred attachment configuration for connecting the adapter 200 to the working channel interface 110. Adapter 200 accepts a forked key 14 into a lateral slot 24. The forked key holds adapter 200 attached to the interface by engaging the undercut sides of fitting 120, The shape of the housing 13 of the apparatus is matched to the shape of the interface 110 and includes side walls extending so as to form a groove or channel 21 which cooperates with the body of the bronchoscope handle to prevent rotation of housing 13. Thus, housing 13 is first positioned so as to envelop the interface 110, and than the forked key 14 is inserted into slot 24 to attach and maintain contact pressure between adapter 200 and the working channel orifice.

FIGS. 3A, 3B and 4 show the combined locking and sealing adapter in more detail. When placed on top of the working channel, its lower surface 22 is pressed against the gasket fitting 120 and seals orifice 125. Lumen 18 is blocked by elastomeric valve 20, preferably implemented as an elastomeric membrane cut along a slit. When the lumen is empty, the slit assumes its normally-closed state, sealing the orifice of the working channel so that suction can be applied via valve 140 to working channel 130 without significant leakage at interface 110. When a tool is inserted through the lumen, the slit is pushed open, allowing the tool to slide through the membrane and into the working channel. The material of valve 20 is preferably sufficiently flexible to form a seal around the inserted tool.

Both elastomeric valve 20 and the elastomeric clamping block are preferably implemented as a unitary elastomeric insert 11 deployed within housing 13. The elastomeric material is preferably flexible material such as rubber or silicon. Insert 11 has a central lumen 18 through which tools may be inserted. The elastomeric clamping block is preferably formed as a substantially cylindrical collar 27 around part of central lumen, thereby defining a central clamping bore for passage of the tool. Collar 27 preferably features at least one inwardly projecting ridge 28 projecting into the central clamping bore to enhance clamping.

Collar 27 preferably has conical surface portions (i.e., sloped steps) 29 around its circumference. Tightening mechanism then preferably includes at least one axially displaceable element deployed for engaging the conical surface 29 so as to apply an inward pressure for clamping the tool within the central clamping bore.

In the implementation illustrated here, as best seen in FIG. 4, flexible insert 11 is retained within housing 13 by two rings, a lower ring 12 and an axially displaceable upper ring 15, both deployed for engaging conical surfaces 29. A screw-nut 16 bears upon the upper ring, displacing it axially downwards. Closing screw-nut 16 pushes the rings one against the other. Downward displacement of lower ring 12 is prevented indirectly by the engagement pressure with fitting 120. The internal surfaces of the rings are oblique, so when the screw is closed and the rings are pushed tighter, it presses the flexible part 11, forcing lumen 18 to narrowed. Narrowing lumen 18 locks the tool placed inside the lumen, preventing it from sliding in or out of the lumen. The lower part of housing 13 has a groove 21, matching the shape of working channel interface 110. It prevents the apparatus from rotating when tightening screw-nut 16.

Figure 5:
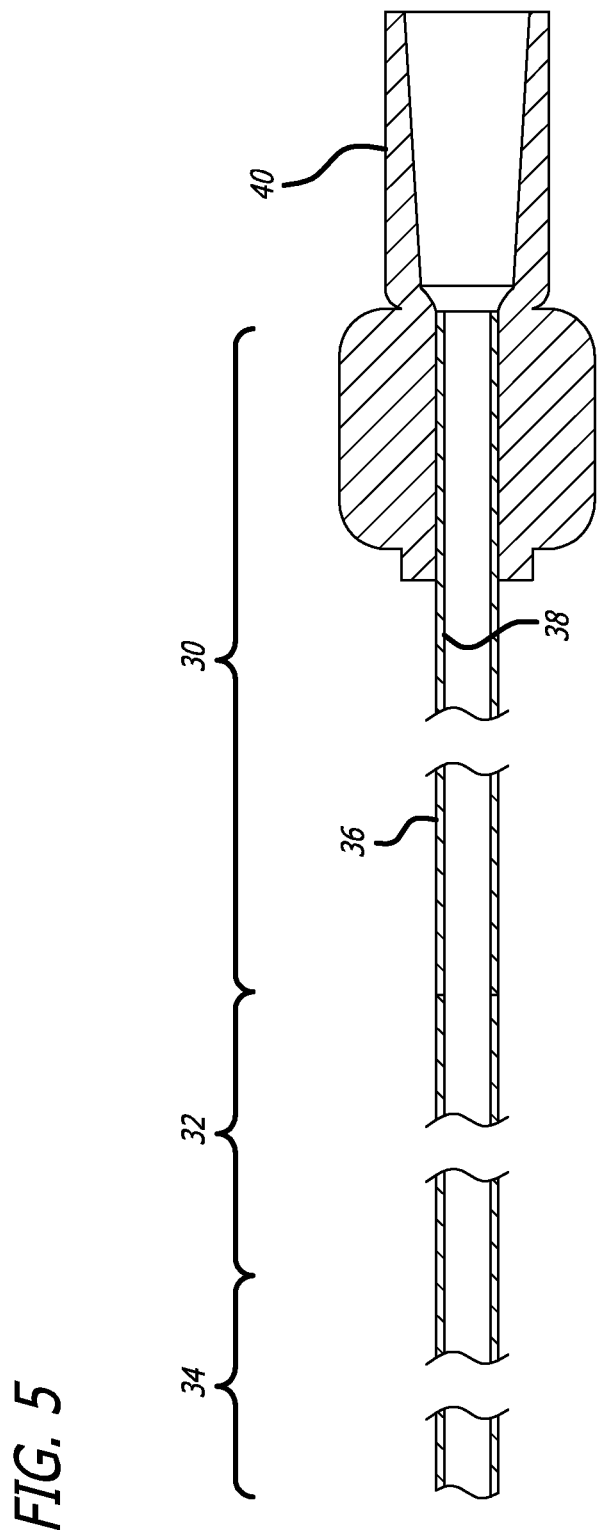
FIG. 5 is a schematic longitudinal cross-sectional view taken through a variable flexibility sheath constructed and operative according to the teachings of the present invention.
Figure 6:
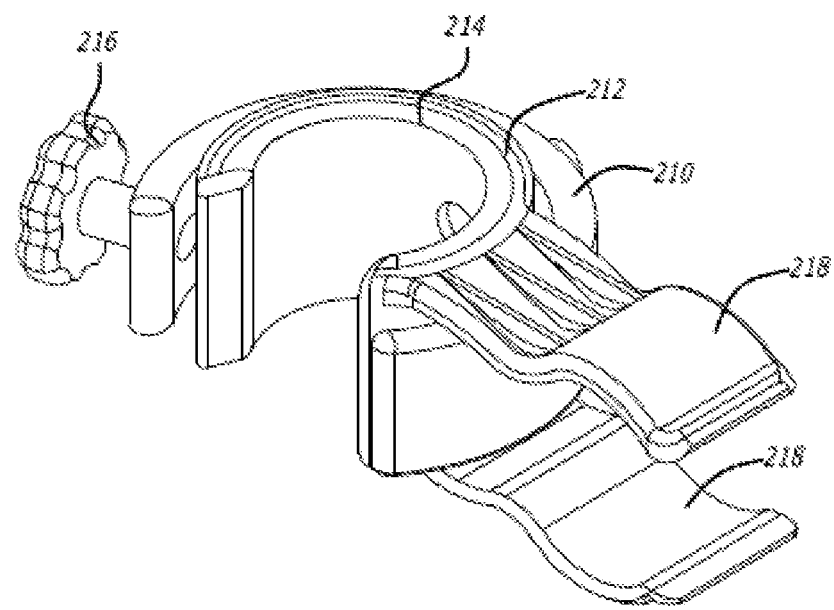
FIG. 6 is an isometric view of a bronchoscope accessory clip constructed and operative according to the teachings of the present invention.
Figure 7:
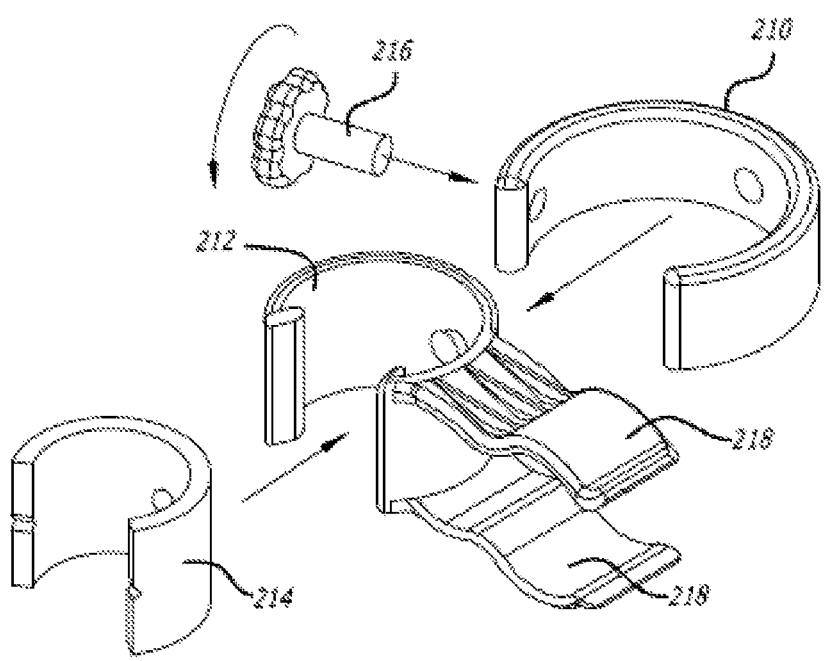
FIG. 7 is a disassembled view of the clip of FIG. 6 indicating the sequence of assembly.
Figure 8:
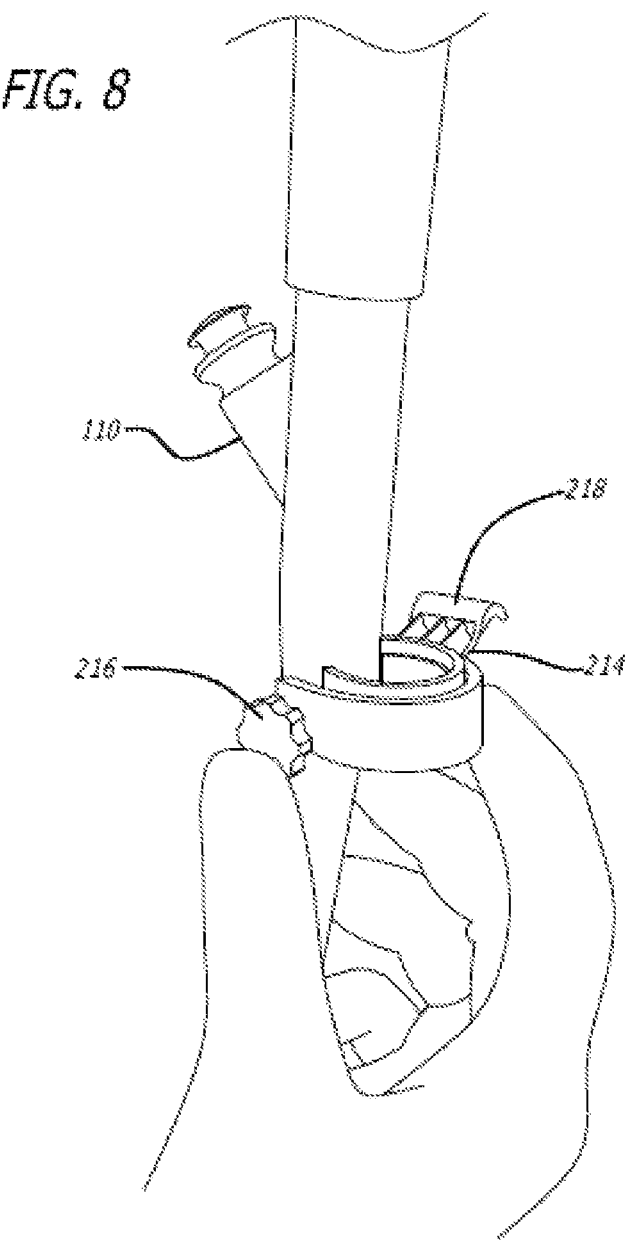
FIG. 8 illustrates mounting the clip of FIG. 6 on a bronchoscope.
Figure 9:
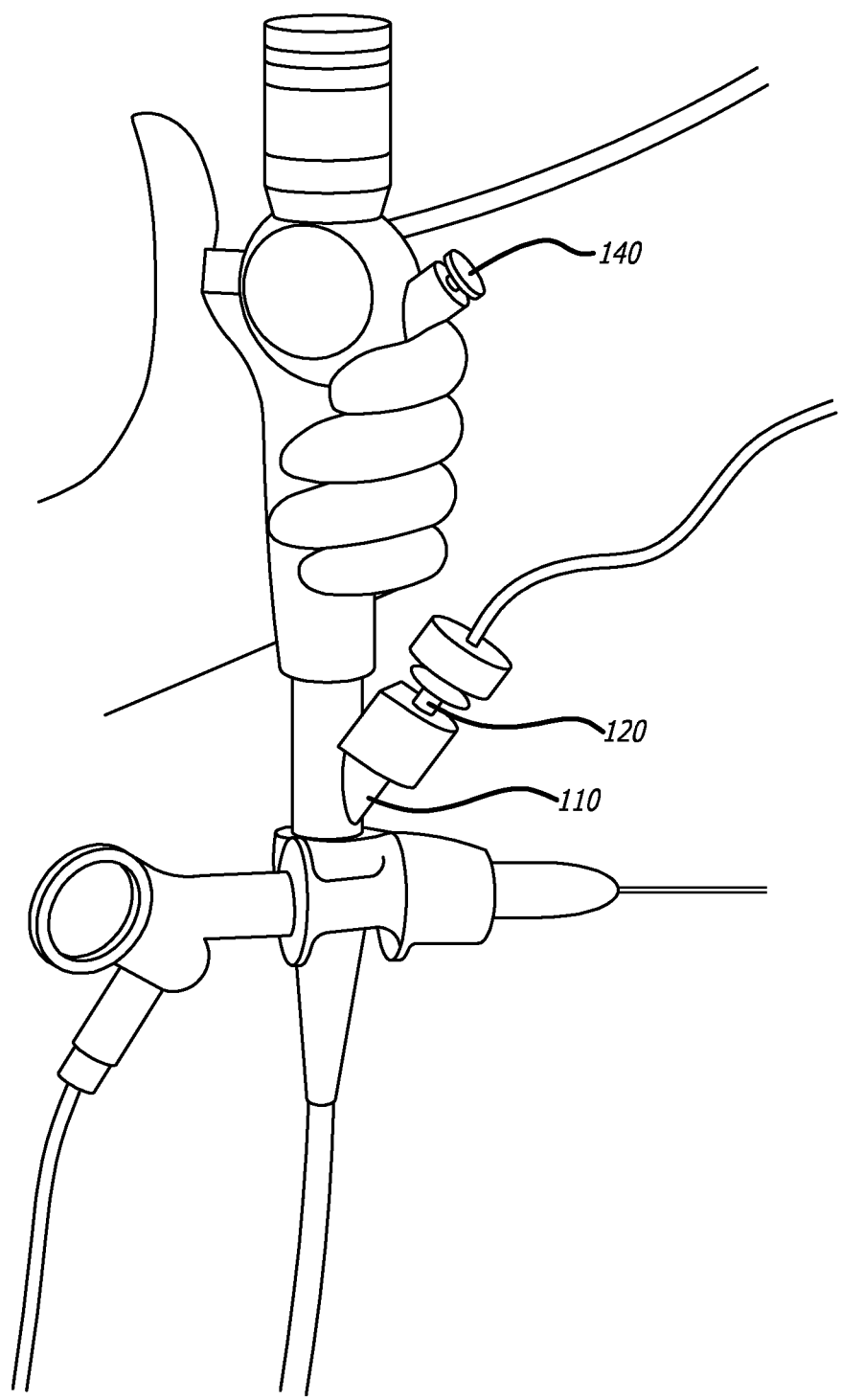
FIG. 9 illustrates the clip of FIG. 6 in use to retain a bronchoscope accessory.
Figure 10:
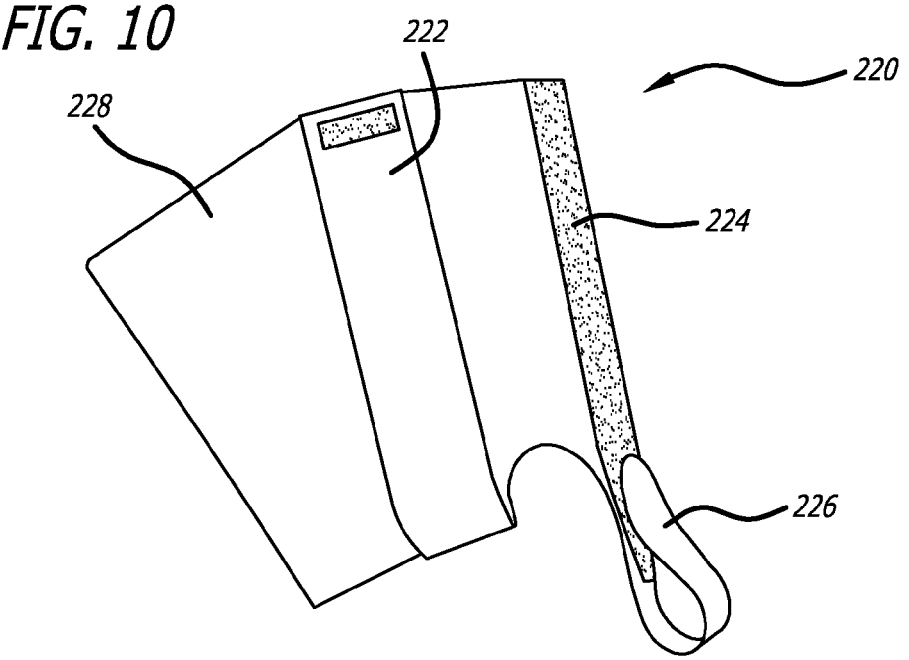
FIG. 10 is a side view of a wrap-around handle extension, constructed and operative according to the teachings of the present invention, in a flattened state.
Figure 11:
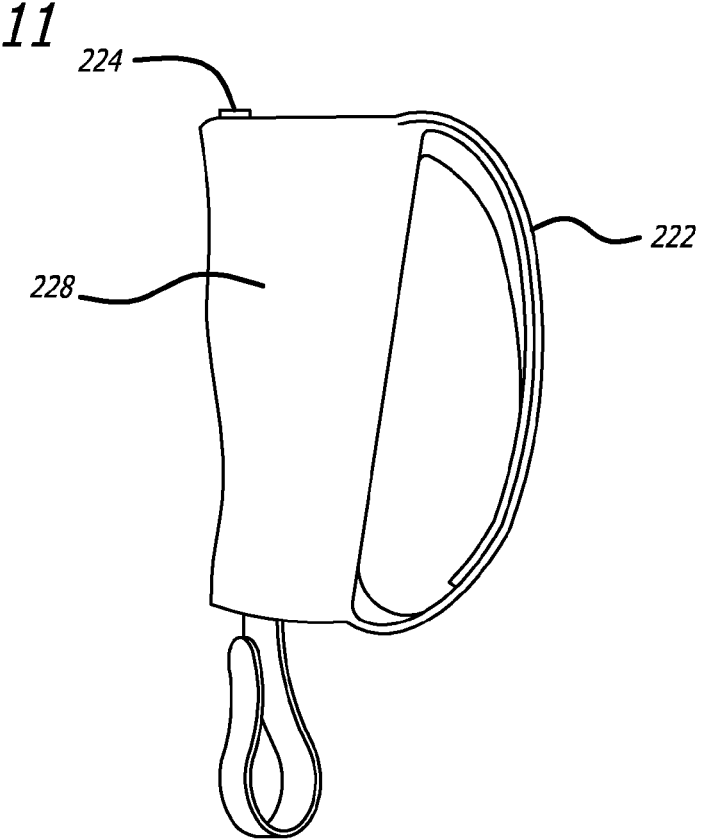
FIG. 11 is a side view of the wrap-around handle extension of FIG. 10 in a deployed state forming a conical sleeve for holding a bronchoscope handle.

Turning now to the second aspect of the present invention illustrated with reference to FIG. 5, this relates to a sheath for use according to the above-mentioned functionality of guiding tools to a point of interest, as described further in the aforementioned PCT patent publication no. WO03/086498. Specifically, it relates to a sheath structure in which the proximal portion 30, i.e., the portion which remains projecting from the bronchoscope handle, is formed with reduced flexibility compared to the primary sheath portion 32. This has been found to greatly facilitate the insertion of various devices, such as for the interchanging of the locatable guide and various tools as mentioned above.

Primary sheath portion 32, which extends along a major portion (and typically more than 80%) of a length of the sheath, is configured by selection of material and dimensions to have a first degree of flexibility suitable for its intended function as is known in the art. Specifically, the primary sheath portion should be sufficiently flexible to negotiate the fine branched structure of the air passageways of the lungs while being stiff enough to allow it to be pushed forwards through passageways and to bend without collapsing the inner lumen.

Reduced flexibility proximal sheath portion 30, on the other hand, has a lower degree of flexibility as measured, for example, by the extent of flexion caused by a given force applied perpendicular to a cantilevered section of the tube at a given distance from the support point. In practical terms, this ensures that the unsupported length of the sheath projecting from the handle of the bronchoscope while in use is relatively stable and doesn't wave about as much as it would if it was as flexible as the primary sheath portion. This facilitates feeding tools etc. into the sheath. The proximal sheath portion and the primary sheath portion together define a contiguous inner lumen. Most preferably, a proximal end piece 40, mechanically associated with a proximal end of proximal sheath portion 30, is shaped to define a conical insertion guide for guiding a tool into the inner lumen, thereby further facilitating insertion of tools etc. into the sheath.

In most preferred implementations, the sheath also has a distal portion 34 which exhibits a higher degree of flexibility than the primary sheath portion to facilitate steering of the sheath via an inserted locatable guide. As a result, the preferred implementation of a sheath according to the present invention exhibits three distinct levels of flexibility.

Structurally, the relatively less flexible proximal portion is preferably implemented by addition of an outer sleeve 36 to the sheath structure. One example of suitable material for a relatively less flexible sleeve is polyamide. Since polyamide is not readily welded to materials typically used for the main portion of the sheath, for example nylon-based materials such as "PEBAX", an implementation as an outer sleeve overlying the inner sheath structure is preferred. The underlying PEBAX structure 38 may optionally be made thinner so that the overall thickness of the sheath does not significantly increase at the less flexible portion. The relatively more flexible distal portion may be implemented by varying the thickness and/or composition of the PEBAX tube, as is known in the art.

Turning now to a further aspect of the present invention, FIGS. 6-9 illustrate a clip according to the invention, and its use. The clip is designed to enable blind attachment and detachment of a bronchoscopic accessory, including, but not limited to, the system of the aforementioned PCT patent publication no. WO03/086498, which is hereby incorporated fully by reference. The clip provides for hands-free retention of the accessory, thereby freeing the practitioner's hand when it is not being actively used. The clip also preferably allows partial or full operation of the accessory from its retained position. The clip mounts on the shaft of the bronchoscope (FIGS. 8 and 9) and does not interfere with normal operation of the bronchoscope.

Structurally, the portion of the clip which attaches to the bronchoscope preferably has a relatively rigid outer bracket 210 for circumscribing at least 180°, and more preferably between about 200° and 250°, around the bronchoscope. Within the outer bracket 210 is mounted a relatively flexible clamping portion 212, typically also circumscribing at least 180°, and more preferably between about 200° and 250°, around the bronchoscope. The clamping portion 212 is typically a "C"-shaped cross-section, i.e., a partial cylinder open along one side. The clamping portion 212 preferably has a resilient lining or insert 214 of material such as silicone which serves to protect the surface of the endoscope and enhance clamping friction. The clamping portion 212 is closed inwards relative to the outer bracket 210 by a tightening mechanism, typically in the form of a tightening bolt 216 as shown. Optionally, outer bracket 210 and clamping portion 212 may be permanently attached or integrally formed on the side remote from the tightening mechanism.

Attached or integrally formed with one or both of the outer bracket 210 and the clamping portion 212 are a pair of resilient jaws 218 which together make the accessory clip. In the example shown here, the resilient jaws are integrally formed with the clamping portion 212 and pass on opposite sides of the outer bracket 210. Most preferably, the form of the accessory clip is configured for clamping a substantially cylindrical body portion of an accessory in an orientation substantially perpendicular to a central axis of the bronchoscope handle/body. This maximizes the accessibility of the accessory device for operation while attached to the clip.

The outer bracket 210, the clamping portion 212 and the accessory clip may be made out of any suitable material, and may all be of the same material or a combination of different materials. Particularly preferred choices of materials include, but are not limited to, stainless steel, aluminum and plastics.

Figure 12:
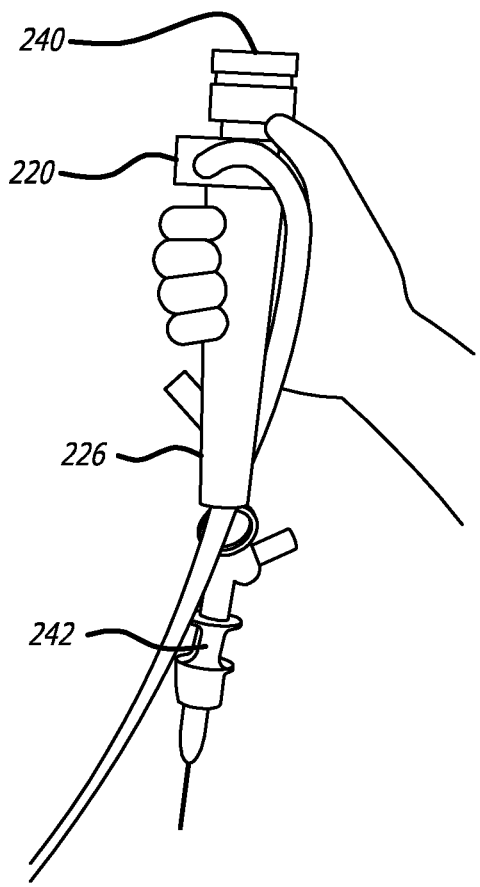
FIG. 12 is a side view illustrating the use of the wrap-around handle extension of FIG. 10 with a bronchoscope and an accessory during a first stage of a procedure.
Figure 13:
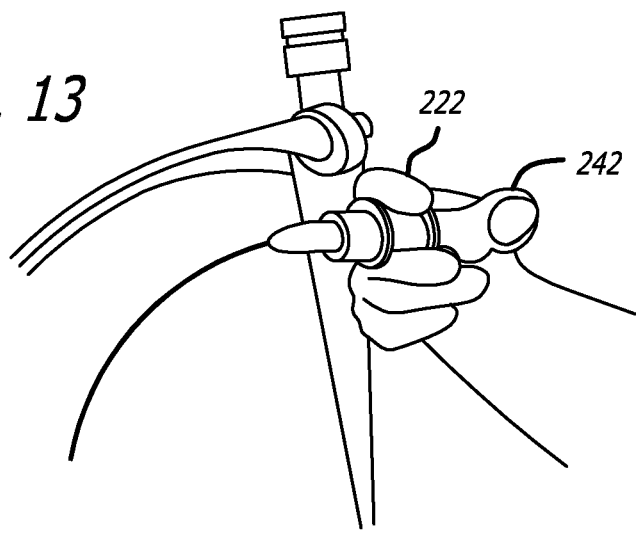
FIG. 13 is a side view illustrating the use of the wrap-around handle extension of FIG. 10 with a bronchoscope and an accessory during a second stage of a procedure.

Turning now to a final aspect of the present invention, FIGS. 10-13 illustrate a wrap-around handle extension 220 for use with a bronchoscope handle. Generally speaking, wrap-around handle extension 220 helps the bronchoscopist in holding with one hand the bronchoscope's handle and concurrently the handle of the bronchoscope tool, and operating the two without them interfering with each other, while leaving the second hand free for any additional required action. To this end, handle extension 220 includes a flexible wrap-around layer 228 provided with complementary fastening arrangements 224 deployed so as to form a conical sleeve (FIG. 11) for holding the bronchoscope handle as shown in FIGS. 12 and 13. Handle extension 220 also includes a hand loop 222 associated with the flexible wrap-around layer 228 and configured for receiving the hand of a user to allow suspension of the conical sleeve from the hand of the user.

Referring to the example illustrated herein in more detail, flexible wrap-around layer 228 is preferably implemented as a thin layer of soft plastic foam. Hand loop 222 is typically formed from similar foam material. Complementary fastening arrangements 224 are preferably implemented as complementary regions of a Velcro fastening arrangement, although other arrangements of straps or fasteners may be used.

Wrap-around handle extension 220 preferably also includes an accessory suspension strap 226 associated with flexible wrap-around layer 228 and configured for suspending an accessory from the conical sleeve (see FIG. 12). Accessory suspension strap 226 is preferably configured with a releasable fastening configuration (for example Velcro) to form a releasable suspension loop. In a particularly preferred implementation as shown here, accessory suspension strap 226 is implemented as an extending tail of one of the Velcro straps of fastening arrangement 224.

As mentioned before, wrap-around layer 228 forms a conical sleeve designed to wrap and fit to the handle of the bronchoscope 240. When the bronchoscope in used for navigation, the bronchoscopic tool 242 is installed hanging in loop 226 as shown in FIG. 12. This allows the bronchoscopist to manipulate the bronchoscope with both hands without being burdened by the bronchoscopic tool, although he is holding that tool as well. When the tip of the bronchoscope reaches to the target, the bronchoscopist put his palm inside the handle 222 so the bronchoscope hangs, or rests, on the back of his hand. Now the bronchoscopist may operate the bronchoscopic tool 242 using his free fingers, as shown in FIG. 13.

The implementation illustrated herein is preferably a single-use disposable accessory. Other similar implementations, using different materials and different techniques for attaching the bronchoscopic tool to the bronchoscope's handle also fall within the scope of the present invention. In each case, the handle extension employs similar principles in that the handle of the tool is suspended in a position that does not interfere with the physician's use the bronchoscope for navigation inside the lungs, and yet after reaching to the target lets the physician operate the bronchoscopic tool using the same hand while still holding the bronchoscope's handle.

Although the above aspects of the present invention have been described in the context of a bronchoscope and bronchoscopic tools, it should be appreciated that other applications using other type of endoscopes and endoscopic tools, in which it is required to hold the tools and the endoscope handle at the same time, also fall within the scope of the present invention.

It will be appreciated that the above descriptions are intended only to serve as examples, and that many other embodiments are possible within the scope of the present invention as defined in the appended claims.

What is claimed is:

1. A clip for receiving a shaft of a bronchoscope, the clip comprising:
   a clamping portion having a C-shape and defining a plane through a center point of the C-shape, the clamping portion including a first arm and a second arm integrally formed with the clamping portion, the first and second arms extending beyond an outer circumference of the C-shape and having a centerline axially aligned with the plane defined by the C-shape;
   a bracket for engaging an outer surface of the clamping portion; and
   an adjustment mechanism operably coupled to the bracket for adjusting positioning of the clamping portion,
   wherein the clamping portion defines a longitudinal axis perpendicular to the plane extending through the center point of the C-shape,
   the clamping portion is configured to secure a shaft of a bronchoscope in an angular orientation relative to the longitudinal axis, and
   the clamping portion is configured to conform about and circumscribe at least 180° of a rounded surface of the bronchoscope.

2. The clip according to claim 1, further comprising an insert for engaging an inner surface of the clamping portion.

3. The clip according to claim 2, wherein the bracket and the insert each have a substantially C-shaped configuration.

4. The clip according to claim 1, wherein the first arm is in opposed relation to the second arm.

5. The clip according to claim 1, wherein the clamping portion is configured to be engaged by the bracket on an outer surface thereof, the adjustment mechanism extending through the bracket to adjust the positioning of the clamping portion.

6. The clip according to claim 1, wherein the clamping portion is configured to receive a shaft of a bronchoscope without impairing a function of the bronchoscope during a surgical procedure.

7. A clip for receiving a shaft of a bronchoscope, the clip comprising:
   a clamping portion having a C-shape and defining a plane through a center point of the C-shape, the clamping portion including a first arm and a second arm, the first and second arms extending beyond an outer circumference of the C-shape and having a centerline axially aligned with the plane defined by the C-shape; and
   an adjustment mechanism for adjusting positioning of the clamping portion;
   wherein the clamping portion defines a longitudinal axis perpendicular to the plane extending through the center point of the C-shape,
   the clamping portion is configured to secure a shaft of a bronchoscope in an angular orientation relative to the longitudinal axis, and
   the clamping portion is configured to conform about and circumscribe at least 180° of a rounded surface of the bronchoscope,
   wherein the clamping portion is engaged by a bracket on an outer surface thereof, the adjustment mechanism extending through the bracket to adjust the positioning of the clamping portion.

8. The clip according to claim 7, wherein the first arm is in opposed relation to the second arm.

9. The clip according to claim 7, wherein the first and second arms are integrally formed with the clamping portion.

10. The clip according to claim 7, wherein the clamping portion is configured to receive a shaft of a bronchoscope without impairing a function of the bronchoscope during a surgical procedure.

11. The clip according to claim 7, further comprising an insert for engaging an inner surface of the clamping portion.

* * * * *